United States Patent [19]

Allen

[11] Patent Number: 5,095,451
[45] Date of Patent: Mar. 10, 1992

[54] CENTRIFUGE PARTICLE SIZE ANALYZER

[75] Inventor: Terence Allen, Hockessin

[73] Assignee: E. I. Du Pont de Nemours and Company, Wilmington, Del.

[21] Appl. No.: 379,463

[22] Filed: Jul. 13, 1989

[51] Int. Cl.$^5$ .................. G01N 23/02; G06F 15/42
[52] U.S. Cl. .................. 364/555; 73/865.5
[58] Field of Search .................. 364/555; 73/865.5; 378/44, 47; 356/373, 335

[56] References Cited

U.S. PATENT DOCUMENTS

| | | | |
|---|---|---|---|
| 3,621,243 | 11/1971 | Olivier | 364/555 |
| 3,982,126 | 9/1976 | Von Alfthan | 378/44 |
| 4,318,180 | 3/1982 | Lundqvist | 364/555 |
| 4,320,415 | 3/1982 | Jones | 364/555 |
| 4,736,311 | 4/1988 | Takeuchi et al. | 364/555 |

Primary Examiner—Parshotam S. Lall
Assistant Examiner—Ellis B. Ramirez

[57] ABSTRACT

The invention provides a method and apparatus for determining particle size distribution of particulate samples. Particle size distribution is determined by measuring particle concentration (based on radiation transmittance measurement) as a function as time, and position along the direction in which the particles are settling. Preferably, the particles in a suspension are subjected to a centrifugal force field by rotation in a disc-shaped settling tank. A radiation source and detector scanning assembly, which is capable of radial movement with respect to the rotating settling tank, measures transmittance through the sample as a function of time and radial position. Also provided are mathematical relations suitable for determining particle size distribution from the measured data.

33 Claims, 20 Drawing Sheets

CENTRIFUGE PARTICLE SIZE ANALYZER

BACKGROUND OF THE INVENTION

Important parameters of particulate or powdered materials include particle sizes and particle size distribution. These parameters affect important physical and chemical properties of the materials, e.g., hiding power of pigments, gloss of paint films, packing properties of powders, sintering properties of metal powders, current leakage through dielectrics.

There are many known procedures for determining particle size and particle size distribution of a particulate sample. A common procedure for determining particle size distribution is to suspend the particulate sample in a liquid medium thereby forming a suspension. The suspension is subsequently subjected to either a gravitational or centrifugal force field. In response to the centrifugal or gravitational force exerted on the particles in suspension, the particles move through the liquid medium. This response to either gravitational or centrifugal force will hereinafter be referred to as settling. Observing the changes in powder concentration within the suspension with respect to time and depth of settling provides information which can be related to particle size distribution. In known centrifugal methods the time-dependent particle size concentrations are observed at a single fixed location relative to the settling chamber or tank.

U.S. Pat. No. 4,736,311 (Takeuchi et al.) discloses an apparatus for measuring particle size distribution which employs a centrifugal force field. In the apparatus there is provided a rotating disc to which a sample vessel is attached at the outer edge. By rotating the disc, a suspension placed within the sample vessel is subjected to a centrifugal force field. On one side of the rotating disc is positioned a fixed light source; on the other side there is positioned a light detector. When the rotation of the disc brings the sample vessel into line with the light source and light detector, a determination of particle concentration at a set point within the sample vessel can be made based on the intensity of light transmitted through the suspension and received by the light detector.

The apparatus is further provided with a centralized processing unit (CPU), random access memory unit (RAM), read only memory unit (ROM), timer, keyboard and display unit. The ROM unit stores equations which relate particle diameter to the time needed for the particle to reach the detecting point. Also, the ROM unit stores equations for correcting the effects of non-parallel particle movement on the observed particle concentrations in the case of either centripetal or centrifugal movement of the particles.

Another system for measuring particle size distribution by subjecting a suspension to centrifugal force is disclosed by U.S. Pat. No. 3,914,604 (Hornby et al.). In this system, the suspension is rotated within an annular chamber located at the periphery of a rotating disc-like member. A beam of electromagnetic radiation is passed through the annular chamber containing the rotating suspension. The particle size distribution is determined by measuring the absorption or scattering of the beam as it passes through the rotating suspension while the powder settles. Errors caused by changes in concentration due to radial motion and by an increase in centrifugal force with distance from the axis of revolution are mitigated by the choice of appropriate dimensions of the electromagnetic beam thickness, radius of the disc and sedimentation distances. The ratio of the thickness, d, of the electromagnetic radiation beam in a direction radial to the radial depth of the beam in the liquid from the radial inner surface thereof, r, is required to be not greater than 0.2. Similarly, the ratio of r to the radius from the center of the disc to the radial inner surface of the liquid, R, is required to be not greater than 0.1.

In the system, the disc is movable with respect to the fixed position of the beam source. However, during measurements of the absorbency or scattering of the beam, the position of the disc relative to the beam source is fixed. Also, as noted above, the choice of the detecting point, i.e., the point where the beam strikes the liquid sample, is governed by the relationship of d/r not being greater than 0.2.

U.S. Pat. No. 3,809,885 (Allen) discloses a device for measuring particle size distribution by subjecting the suspension to either a centrifugal or gravitational force field. The apparatus comprises a sedimentation tank, an isotope X-ray source on one side of the tank and a proportional counter operating as a detector on the opposite side of the tank. The X-ray source and counter are movable with respect to the tank whereby measurements of absorbency can be taken at different depths.

In one embodiment of the apparatus there is provided a disc-shaped tank which can be rotated. The suspension can thus be monitored with an X-ray beam at a known distance from the center. Also, the X-ray source and detector can be moved radially so that the single position of detection for taking the measurements for a particular distribution determination can be selected among a continuum from the center of the tank.

SUMMARY OF THE INVENTION

It has been discovered that the time required for determining particle size distributions can be drastically shortened by making concentration vs. time measurements on settling particles as a function of position along the direction of motion of the particles. Thus, for example, the present invention provides, inter alia, a method and apparatus for determining particle size distribution in a suspension subjected to a centrifugal force field, by making measurements as a function of transmitted beam intensity, time and radial position, e.g., using an X-ray beam. Furthermore, the invention relates to a method and apparatus for determining particle size distribution wherein a beam source and detector are capable of scanning radially with respect to a rotating sample. In addition, the invention relates to a method and apparatus for determining particle size distribution utilizing radial position as a variable, which permits particle size distribution to be determined in a much shorter time period. Mathematical procedures have been determined which permit translation of beam intensity vs. time vs. position measurements into accurate particle size distribution data.

Briefly, one aspect of the invention comprises a settling tank, preferably disc-shaped, which is capable of being rotated in order to induce a centrifugal force field, a scanning radiation detection system capable of movement along a radial direction, and associated computer means for data storage, analysis and output. The latter includes the calculated particle size distribution in terms of mass undersize, a highly useful parameter in particle technology. Mass undersize is defined as the mass percentage of the total sample which is below a given diameter.

According to one aspect of the invention, a radiation source and detector are mounted on opposite sides of a disc-shaped settling tank. The intensity of a beam, e.g., an X-ray beam, passing through the suspension containing the particle sample is detected and recorded at predetermined settling times and radial positions of the disc-shaped tank. To provide for rapid analysis, the settling tank is rotated and thus acts as a centrifuge. The intensity/position/time data are analyzed using newly developed formulas to rapidly determine mass undersize. Through the incorporation of the radial position parameter, the invention provides for a particle size analyzer and method for determining particle size distribution which are more efficient than known analyzers and determination procedures.

Accordingly, in one aspect, the invention comprises a method for determining the particle size distribution of a set of particles comprising:

measuring a parameter correlated with the concentration of particles in a sample of said particles which are settling under the influence of gravity and/or a centrifugal force, said parameter being measured at at least two different positions which lie along the direction of motion of said settling particles, and correlating said measurements with said particle size distribution.

Alternatively, the concentration gradient can be determined using a linear detector array or an x-ray strip detector, rather than a mechanically scanning apparatus. The particle size distribution would be generated using the same method, and the information necessary for the calculations would be selected from the data gathered.

In preferred aspects, said parameter is the extent of X-ray transmission through said sample at said positions and times; said particle sample is suspended in a rotating suspension fluid whereby the particles are subject to centrifugal force, and wherein said positions are along a direction radial to the axis of rotation of said fluid; and each X-ray transmission measurement is at a different radial position.

A preferred method comprises:

(a) radially scanning a suspension of dispersed particles under a centrifugal force field by passing a beam of radiation from a radiation source through said suspension while moving said radiation source and an associated radiation detector for receiving said beam in a radial direction with respect to said chamber, said radiation source and radiation detector being positioned on opposite sides of said chamber, and said radiation detector continually generating radiation transmission data;

(b) delivering said data to a computer having stored therein a program for determining particle size distribution from said data; and (c) determining a mass undersize particle size distribution by said program in accordance with the relationship:

$$F(D_m) = \int (r_i/s)^2 dQ$$

wherein

Q is the radiation density of the suspension at time $t_i$ and radius $r_i$ and is determined from the Lambert-Beer law, $D_m$ is the largest particle diameter in the area of the beam at time t and detection position $r_i$, and $F(D_m)$ is the fractional mass smaller than $D_m$: and wherein $D_m$ and Q at $r_i$ are determined, respectively, using the following equations:

$$I_t = I_c \exp(-Bc)$$

$$Q = \log_{10}(I_c/I_t)$$

$$(D_m)^2 = \frac{18\eta \ln(r_i/s)}{(\rho_s - \rho_f)w^2 t}$$

wherein $I_t$ is the measured intensity of the emerging beam, $I_c$ is the intensity of the emerging beam when the settling tank is filled with a clear liquid, c is the concentration of the particulate sample in the portion of the suspension which is within the area of the beam, B is a constant, $\rho_s$ is the density of the powdered material, $\rho_f$ is the density of the liquid medium, w is the radial velocity of the settling tank, $\eta$ is the viscosity of the liquid medium, s is the radial distance from the center of the settling tank to the surface of the suspension, $r_i$ is the radial distance from the center of the settling tank to the point of detection at $t_i$, and $t_i$ is the time of detection.

The apparatus aspect of the invention comprises an apparatus for determining the particle size distribution, $F(D_m)$, of an assembly of particles settling along a certain direction comprising, a radiation source and detector combination for measuring the transmittances of said radiation through said settling particles at selected positions along said direction, and a computer programmed to calculate said particle size distribution from said measured transmittances in accordance with the relationship:

$$F(D_m) = \int p_i^2 dQ$$

wherein $D_m$ is the largest particle diameter in the area of the beam at time $t_i$ and detection position $r_i$;

$p_i$ is the relative position (unitless) of each measurement i; and

Q is the radiation density of the suspension at time $t_i$ and radius $r_i$.

The methods and apparatuses according to the invention can be utilized for determining particle size distribution of particulate samples containing particles within a wide range of sizes. Generally, when X-rays are employed, the invention is suitable for determining the particle size distribution of samples having particle sizes within the range of about 0.05–100 micrometers. In the centrifugal mode, the particle sizes are preferably in the range of 0.1–10 micrometers and in the gravitational mode the particle sizes are preferably in the range of 1.0–80 micrometers. For other wavelengths, the same particle size ranges can be determined, but the generated intensity distribution must be modified to determine a size distribution.

The invention can be utilized to determine the particle size distribution of any particulate material as long as it is essentially inert to, e.g., photochemically inert, and not transparent to the radiation employed. The particles can be porous. The particles can be of any shape, regular or irregular, and can be firm or soft. The numerous materials which can be analyzed include particulate inorganic materials, in particular, metal oxides, such as titanium dioxide and chromium dioxide.

There must be a finite density differential between the particles and the suspension fluid in order to permit settling. Thus, while the particle density can vary greatly, the difference between the particle density and fluid density must be sufficient enough to allow settling to occur. To ensure that settling occurs, the suspension liquid is selected so as to be less dense than the particles to be analyzed. By way of example, the typical density range for $TiO_2$ particles is about 4 to 5 $g/cm^3$, whereas the density of water is, of course, generally about 1 $g/cm^3$.

In order for analyses to be performed, the particulate sample must have a sufficient concentration to absorb or scatter a measurable factor of the incident beam. The concentration should be high enough to attenuate the beam but low enough to prevent particle-particle interference from adversely affecting the measurements. Preferably, the concentration is sufficient to absorb or scatter at least about 10% of the incident beam, especially 20-30%.

The actual range of suitable concentrations will depend on several factors including the nature of the material of the particulate sample, the size distribution of the sample and the type of radiation being used. Generally, the concentration of the particles in the suspension can vary within wide limits, for example, about 0.01–4 vol.%, preferably about 0.1–3 vol.%, especially about 0.1–1.0 vol.%. For X-rays, it is preferable for the concentration to be less than about 0.2 vol.% in order to prevent hindered settling (i.e., particle-particle interference). For optical radiation, i.e., visible, ultraviolet and infrared, the concentration preferably is about 0.01–0.1 vol.%.

During particle size distribution analysis, the samples are typically in the form of a suspension in a fluid. Preparation of the suspensions can be by any conventional method, such as adding liquid containing a dispersing agent to the powder under agitation followed by sonification for one to five minutes.

The viscosity of the fluid must be such that it does not adversely affect movement of the particles within either a gravitational or centrifugal force field in a manner which would prevent adequate determination of the particle size distribution. Preferably, the viscosity of the fluid is selected so that the particles will settle at least about 1 mm from the starting position during the analysis. The viscosity of the fluid is selected based on the particle being analyzed. As mentioned above, the only really important criterion is that the viscosity should be such that the particles settle at least 1 mm during an analysis time deemed acceptable. Preferably, the viscosity of the fluid is about 0.5 centipoise to 1.0 poise.

The fluid medium should be inert with respect to the material of the sample. Also, absorbance of the radiation by the liquid should be minimized, to not adversely affect the capability to determine particle concentrations by measurement of transmitted beam intensity. The many suitable liquids include, but are not limited to, water, water-glycerine mixtures, cyclohexanol, ethylene glycol and ethanol. For metal oxides, the most suitable liquid medium is cyclohexanol.

The radiation must be one which is absorbed or scattered by the solid particles of the suspension so that there will be a detectable difference between the incident beam and the transmitted beam. Generally, the absorbance mechanism is irrelevant as long as particle integrity is maintained. In essence, any type of radiation can be utilized. For example, suitable radiation includes visible, ultraviolet, infrared, X-ray, and gamma ray radiation.

Virtually, any wavelength of electromagnetic radiation is suitable so long as it will provide test data. X-rays are preferred, since the attenuation is directly proportional to the mass of the particles in the beam. For health reasons and ease of cooling, soft X-rays (longer wavelengths) are usually preferred. In addition, a low cooling requirement simplifies the radial movement of the radiation source and detector assembly. A suitable X-ray source is a beryllium crystal and tungsten target. Examples of commercially available X-ray tubes are the TF3005, XTF5020, and XTF5010 models by X-Tech. The Bicron model, 0.5xM.040Q/1.5BLP-X, is an example of a suitable commercially available detector assembly.

The materials used for manufacture of the settling tank, which is preferably disc-shaped, are selected so that their absorbency does not adversely affect the beam intensity analysis. Preferably, the materials used to make the settling tank are essentially transparent with respect to the beam and typically exhibit a beam transmission of substantially more than 50%. Suitable materials include, but are not limited to, acrylics, polyvinyl acetates, polyethylene and polyvinyl chloride. In the case of X-rays, aluminum which is transparent to X-rays is also a suitable material.

To enhance accuracy of concentration measurements, a beam should interrogate many particles. The parameter X-ray flux is the product of beam area times the intensity. So, the preference is for a large area beam. However, measurement precision falls as beam width increases so a narrow beam is best for high precision. A compromise is to use a 1 mm wide beam 7 mm from the surface for no loss of precision. In one embodiment of the invention, scanning is performed 3 mm from the surface so the ideal beam width would be 3/7 mm, but this reduces the flux to an unacceptable level. A solution is to use an arc of radiation, not a circle. The beam diverges widely, but since the receiver is an arc of the same dimension as the beam, this effectively collimates the beam. For a helpful discussion on these and other aspects of determining particle size distribution, see T. Allen, *Particle Size Measurement*, 3rd Edition, Chapman and Hall (1981).

As to other aspects of the analysis procedure, centrifuge speed is generally about 500–10,000 rpm; the distance between source and detector is, of course, greater than the width of the settling tank but preferably less than about 4.0 cm, especially less than 3.5 cm; and measurement is continuous. An example of the scanning procedure is to scan at a rate of about 0.1 mm/min. for a time period of 7 minutes, yielding a total scanned distance of 0.7 mm. An important aspect of the invention which results in a major advancement in the field of powder technology is the manner in which the data collected in conjunction with the foregoing is analyzed. The invention provides for an analysis of particle size distribution which takes into account not only the variables of time and particle concentration (based on beam intensity), but also the radial position of the point of detection as discussed above. As is well known, the Beers-Lambert law establishes a relationship between the intensity of the emerging beam and the concentration of the powder in the beam for a homogeneous suspension:

$$I_t = I_c \exp(-Bc) \qquad \text{5}$$

wherein $I_t$ is the measured intensity of the emerging beam,
$I_c$ is the intensity of the emerging beam when the settling tank is filled only with the liquid medium chosen for formation of the suspension,
c is the concentration of the powder in the beam, and
B is a constant.

Also well known is Stokes' law which permits calculation of the diameter of the largest sized particle, $D_m$, present in the measurement zone, i.e., the area of the suspension within the beam, at a radius r and a time t:

$$(D_m)^2 = \frac{18\eta \ln(r_i/s)}{(\rho_s - \rho_f)w^2 t_i} \qquad \text{II}$$

wherein $\rho_2$ is the density of the particulate material,
$\rho_f$ is the density of the liquid medium,
w is the radial velocity of the settling tank,
$\eta$ is the viscosity of the liquid medium,
s is the radial distance from the center of the settling tank to the surface of the suspension,
$r_i$ is the radial distance from the center of the settling tank to the point of detection, and
$t_i$ is the time of the measurement.

The parameter of interest, percentage undersize, also known as mass undersize, can be related to both concentration and largest particle diameter, $D_m$, at a given time and radial position in accordance with this invention, using Kamack's equation which can be expressed for this invention as follows:

$$F(D_m) = \int (r_i/s)^2 dQ \qquad \text{40}$$

wherein

Q is the radiation density of the suspension at time $t_i$ and radius $r_i$, $Q = \log_{10}(I_c/I_t)$ (at $t=0$, $Q=1$, which refers to 100% of the initial concentration),
$D_m$ is the largest particle diameter in the area of the beam at time $t_i$ and detection position $r_i$, and
$F(D_m)$ is the fractional mass smaller than $D_m$.

From these equations, a general solution in recursive form can be obtained:

$$F_i = (y_i + y_{i-1,i})Q_i/2 + \sum_{j=1}^{i-1}\left[\frac{y_i + y_{i-1,i}}{y_{j+1,i} + y_{j,i}} - \frac{y_i + y_{i-1,i}}{y_{j,i} + y_{j-1,i}}\right]F_j \qquad \text{IV}$$

wherein $y_i$ is $(r_i/s)^2$;
$r_i$ is the radial distance to the point of detection at time $t_i$;
$y_{j,i}$ is $y_j(D_j/D_i)^2$
$y_{j,i}$ is $y_i$;
$y_{0,i}$ is 1;
$D_i$ is the largest particle diameter in the area of detection at position $r_i$ and time $t_i$;
n is the number of data points selected;
i is an integer from 1 to n; and
$F_i$ is the percentage of mass of the particulate sample which has a diameter smaller than $D_i$.

The values obtained for $D_i$ and $F_i$ define the mass undersize curve.

A similar procedure can be followed using another form of Kamack's equation.

$$F(D_m) = \int p_i^2 dQ \qquad \text{V}$$

wherein $D_m$ is the largest particle diameter in the area of the beam at time t and detection position $r_i$;
$p_i$ is the relative position (unitless) of each measurement i; and
Q is the radiation density of the suspension at time $t_i$ and radius $r_i$.

BRIEF DESCRIPTION OF THE DRAWINGS

Various other objects, features and attendant advantages of the present invention will be more fully appreciated as the same becomes better understood when considered in conjunction with the accompanying drawings, wherein.

DETAILED DESCRIPTION

Figure 1:
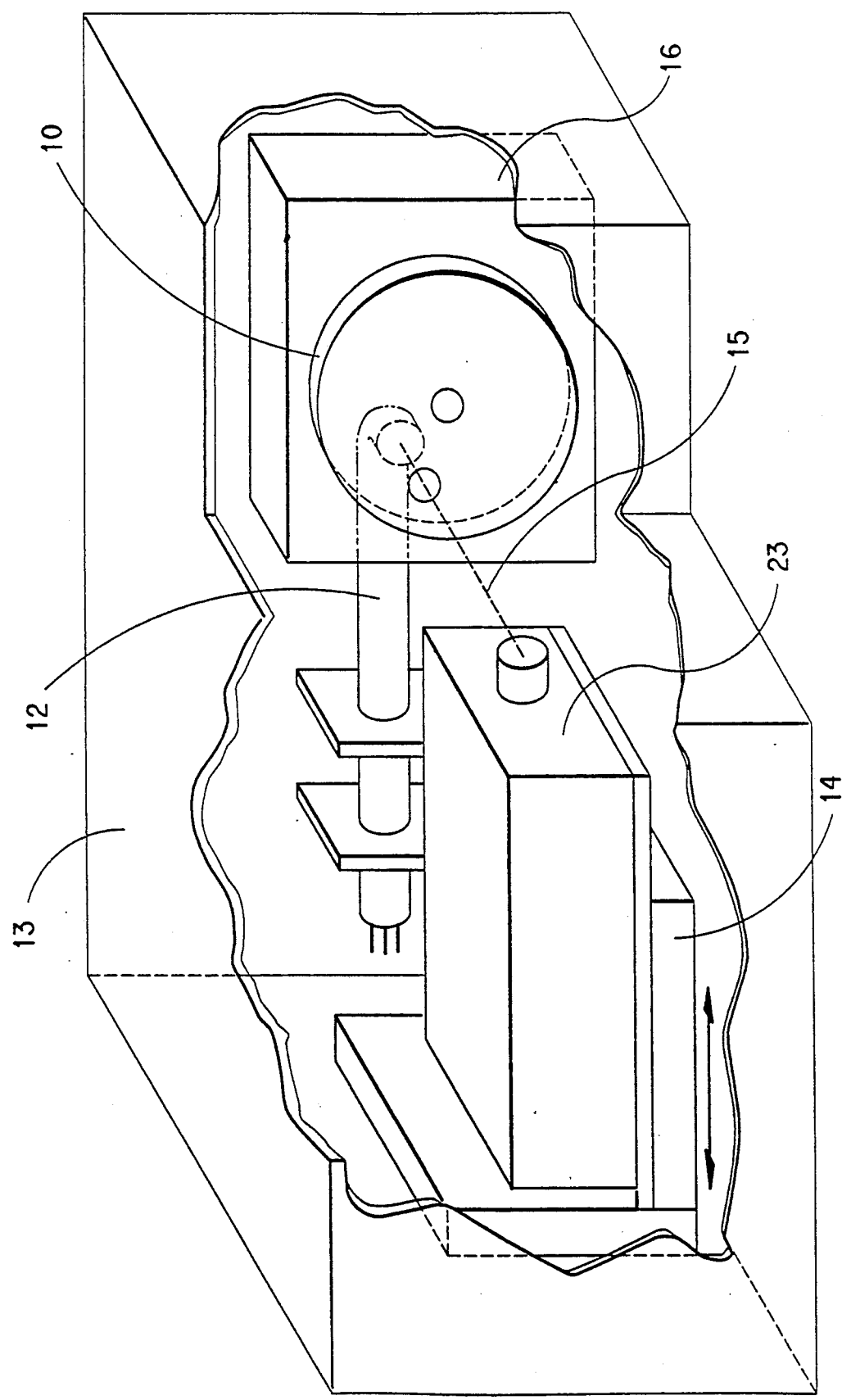
FIG. 1 is a side view of the preferred apparatus of the invention.
Figure 2:
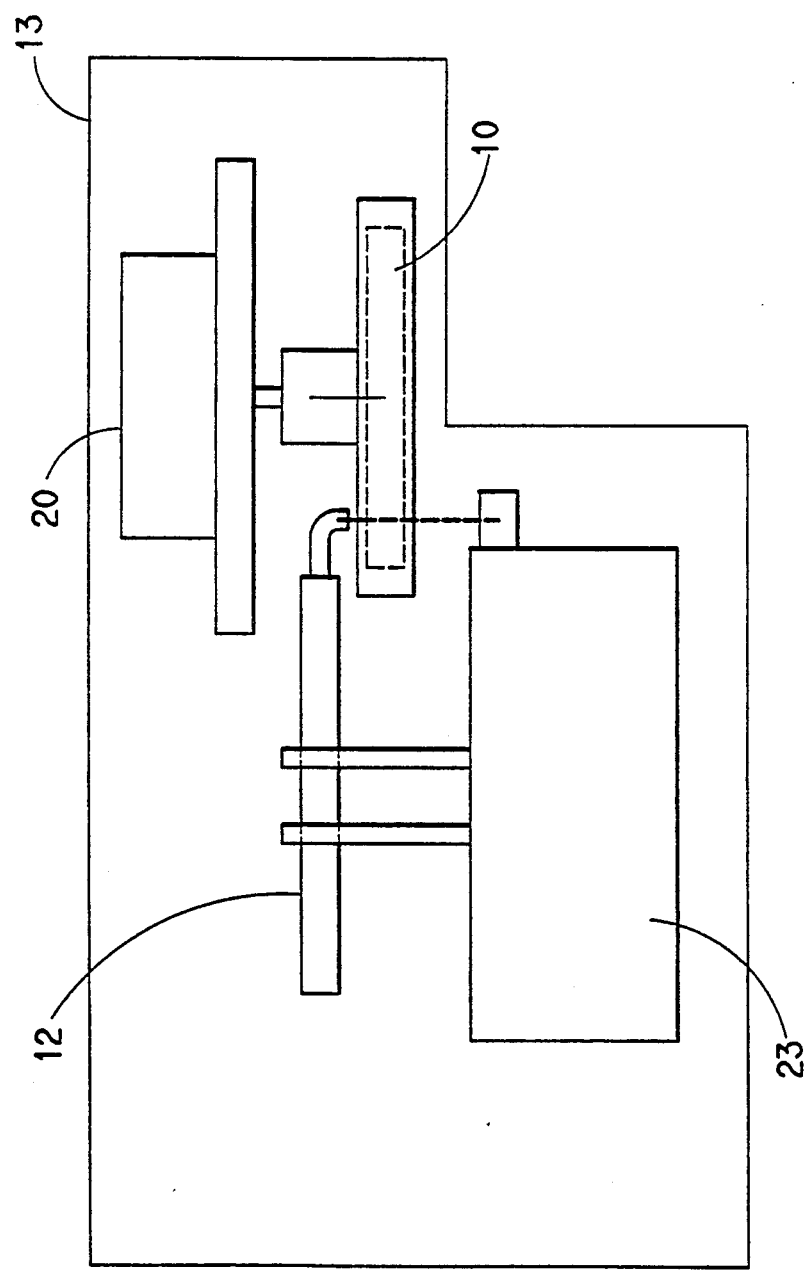
FIG. 2 is a top view schematic of the apparatus of FIG. 1.
Figure 3:
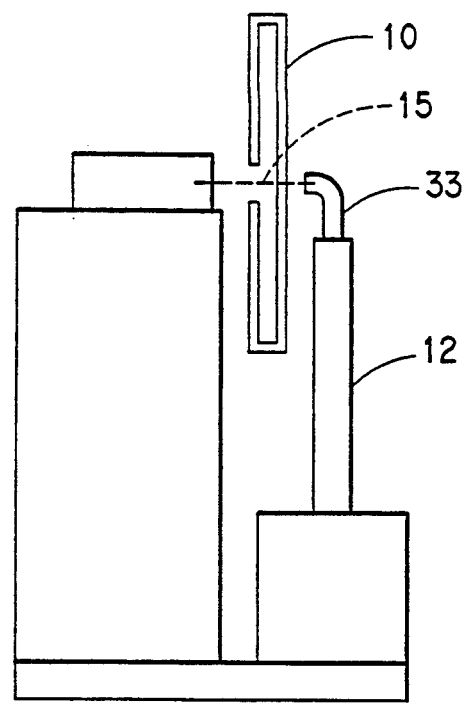
FIG. 3 is a bottom view schematic of the apparatus of FIG. 1.

A preferred embodiment of the invention, FIG. 1, comprises a vertically mounted disc-shaped settling tank 10 equipped with an X-ray tube 23 including an X-ray tube source 11 and corresponding detector 12 housed in a casing 13. The X-ray beam 15 passes through the settling tank. As can be seen in FIG. 2, the apparatus is further equipped with a motor 20, used to spin the settling tank 10, thereby causing the tank to act as a centrifuge. For this reason, a settling tank housing 16 is also provided. The detector 12 and X-ray tube 23 are mounted on a single platform 14, on opposite sides of the settling tank. The platform 14 is driven by a lead screw, thereby allowing the source and detector to simultaneously move together along the radius of the tank, scanning from the outer edge of the tank to the center. The source and the detector scan in the direction of the double-headed arrow as shown in FIGS. 1 and 2. The X-ray beam 15 as shown in FIG. 3, passes through the settling tank 10 into a quartz light pipe 33, and then into detector 12.

In order to carry out a gravitational mode, the motor 20 is not used, and the vertically mounted tank remains stationary. In the gravitational analysis, it is preferred to scan in an upward direction from a point below the axis of rotation of the centrifuge. This configuration is also advantageous for determining $I_{min}$ for a centrifugal analysis when large (micrometer size) particles are present in the suspension.

Figure 4:
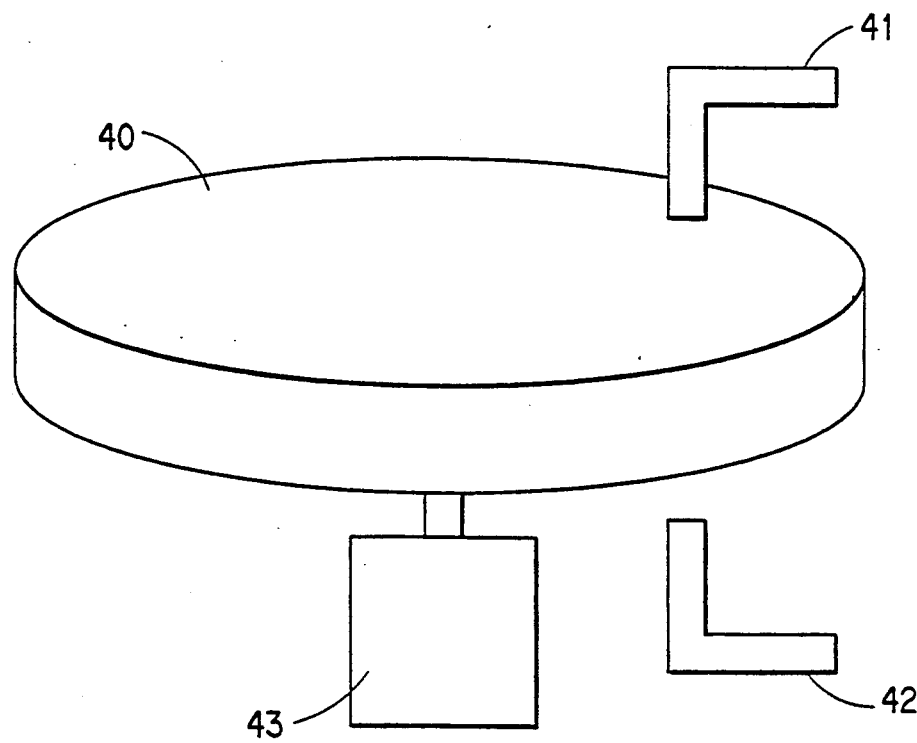
FIG. 4 is an alternate apparatus of the invention.
Figure 5:
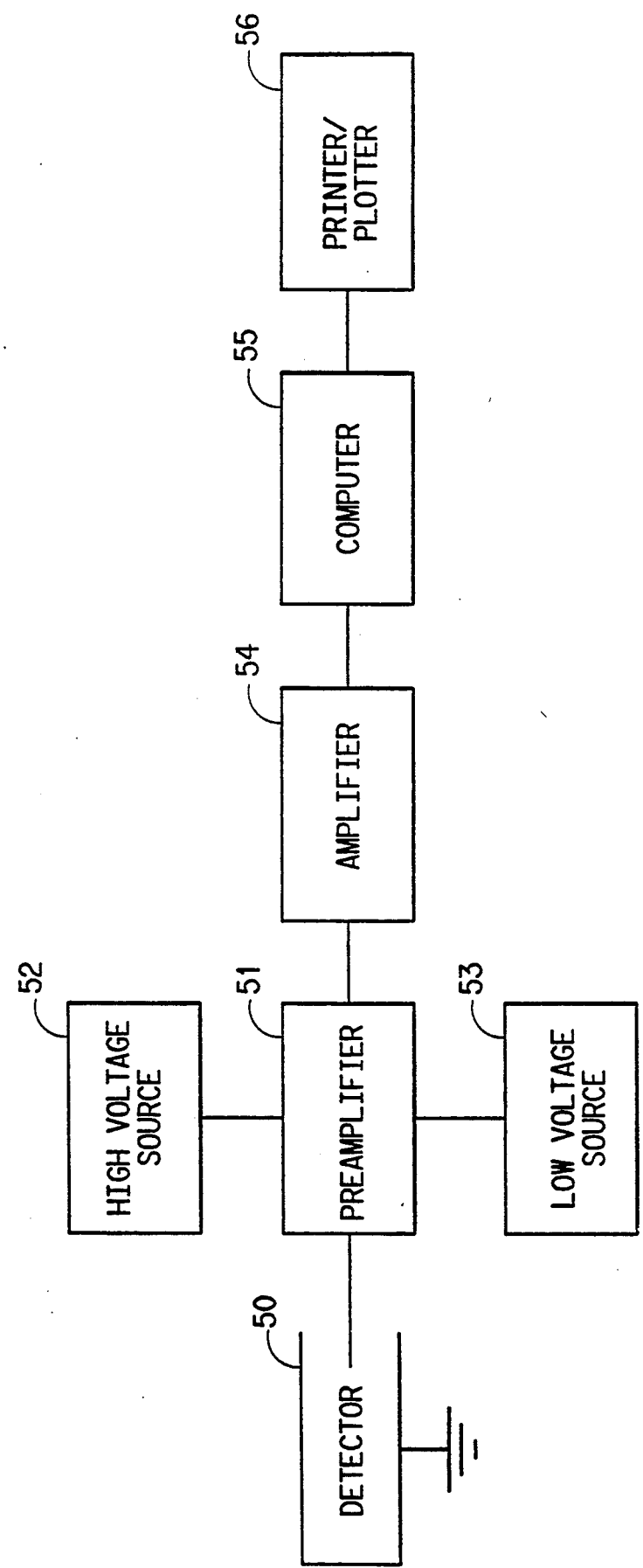
FIG. 5 is a block diagram of associated electrical circuitry.

An alternative arrangement is shown in FIG. 4. The tank 40 is mounted horizontally with X-ray tube source 41 and detector 42 again mounted on opposite sides of tank 40. A motor 43 is required to spin the settling tank and induce a centrifugal force field. In both the horizontally and vertically mounted models, it is important that the settling tank have a low X-ray absorption rate. An X-ray tube is preferred because it is capable of being turned off when not in use so the health risks associated with it are minimized. In addition, the stability is adequate and mounting presents no significant problems.

With the detector at radius $r_0$ and scanning at a constant speed to an inner radius $r_1$ at time $t_1$, and with the initial concentration of particles suspended in the liquid medium, $Q=1$ (i.e., 100% of initial concentration) then the equation relating percentage undersize (commonly referred to as Mass Undersize) and concentration is given per the above by Kamack's equation:

$$F(D_m) = \int (r_i/s)^2 dQ \qquad \text{III}$$

Figure 7:
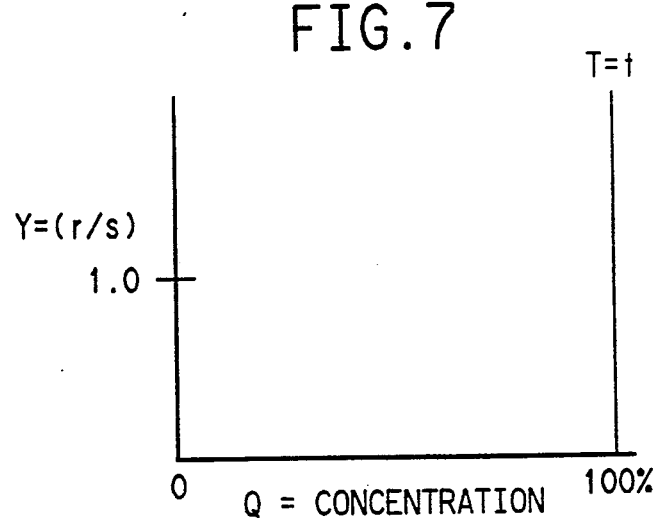
FIGS. 7-11 represent the build-up of the position versus concentration curves.

If Q is plotted as a function of $y_i = (r_i/s)^2$ with $t_i$ as a parameter, a family of curves is obtained whose shape depends upon the size distribution function. Referring to FIG. 7, the boundary conditions are that $Q_0 = 1$ (i.e., 100%) when $t_i = 0$ for all $y_i$ and that $Q = 0$ for $r_i = s$ (i.e., $y_i = 1$) when $t > 0$. This is based on an assumption that at $t > 0$ all the particles will have moved from the radial position s. Hence, all the curves except for $t = 0$ will pass through the point (0,1). Note that the detector scans from the outer radius inward, therefore, $t_1 > t_2 > t_3 > t_4$, etc. and $r_1 < r_2 < r_3 < r_4$, etc.

Figure 8:
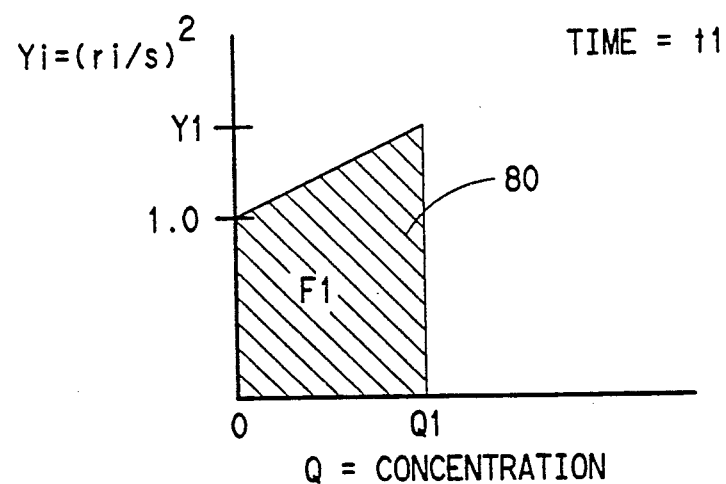

If the detector is positioned at radius $= r_1$ at time $t_1$, the concentration $Q_1$ is measurable. Two points are now known for time $= t_1$; (0,1.0) and $(Q_1, y_1)$. For purposes of the evaluation, the relationship is assumed to be linear as represented by FIG. 8. From Equation III, the area under the curve (80) is equal to the percentage mass of particles under size $D_1$, or Mass Undersize. This area approximates a trapezium, and can be expressed as:

$$F_1 = (1 + y_1)Q_1/2 \qquad \text{VI}$$

The relevant Stokes diameter (i.e., the largest diameter particle present at location $r_1$ at time $t_1$), given by Equation II, is:

$$D_1^2 t_1 = \frac{9\eta \ln (r_i/s)^2}{(\rho_s - \rho_f)w^2} \qquad \text{VII}$$

or, substituting $y = (r/s)^2$ and $$k = \frac{9\eta}{(\rho_s - \rho_f)w^2};$$

$$D_1^2 t_1 = k \ln y_1 \qquad \text{VIII}$$

Figure 9:
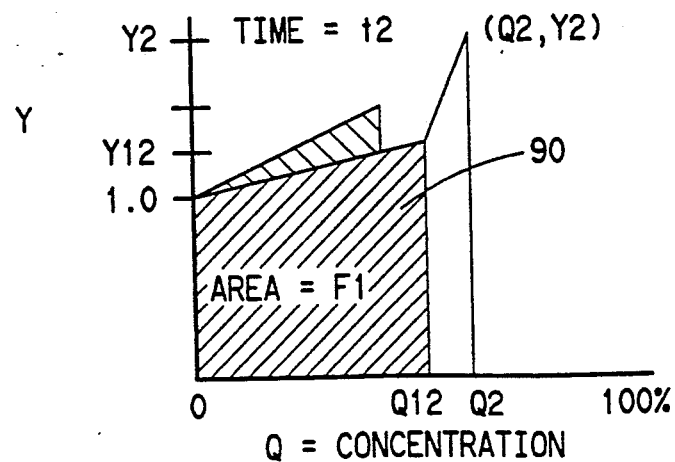

The next concentration reading used in the evaluation, $Q_2$, is measured at time $t_2$ and radius $r_2$. Again, only two points are known on the time $= t_2$ curve; (0,1) and $(Q_2, y_2)$. There is, however, some unknown radius at time $t_2$ where the largest particle present will be of size $D_1$. Referring to FIG. 9, that condition is denoted as the point $(Q_{12}, y_{12})$, but the values of these points are unknown.

The area under this curve (90) again represents the mass of particles under size $D_1$. This was previously defined as $F_1$. From Equation VIII, the following are obtained:

$$D_1^2 t_2 = k \ln(y_{12}) \text{ and } D_2^2 t_2 = k \ln(y_2),$$

hence:

$$y_{12} = y_2^{(D_1/D_2)^2} \qquad \text{IX}$$

Also, equating areas;

$$F_1 = (1 + y_1)Q_1/2 = (1 + y_{12})Q_{12}/2$$

or:

$$Q_{12} = \frac{(1 + y_1)}{(1 + y_{12})} Q_1 \qquad \text{X}$$

Figure 10:
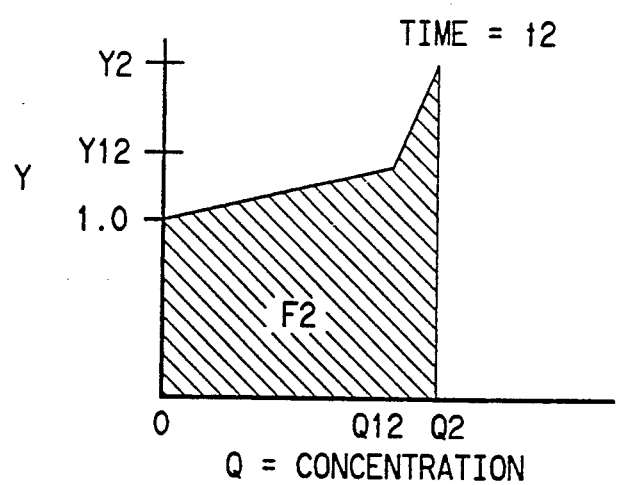

Thus, both $y_{12}$ and $Q_{12}$ may be calculated using information gathered at time $t_1$ and $t_2$. This allows the curve for time $= t_2$ to be refined slightly from the earlier linear relationship. The curve for $t_2$ is now approximated by the three points (0,1.0), $(Q_{12}, Y_{12})$ and $(Q_2, Y_2)$. The corresponding area below is defined as $F_2$, FIG. 10. Note that $F_2$ encompasses $F_1$. By the trapezoidal rule:

$$F_2 - F_1 = (y_2 + y_{12})(Q_2 - Q_{12})/2 \qquad \text{XI}$$

Substituting for $Q_{12}$ from Equation X and rearranging the equation gives the parameter of real interest, mass undersize, $F_2$:

$$F_2 = (y_2 + y_{12}) Q_2/2 + \left[1 - \frac{y_2 - y_{12}}{y_{12} + 1}\right] F_1 \qquad \text{XII}$$

As can be seen, it is not actually necessary to physically calculate $Q_{12}$ to determine $F_2$.

Proceeding in a similar manner, for time $t_3$;

$$D_1^2 t_3 = k \ln y_{13}$$

$$D_2^2 t_3 = k \ln y_{23}$$

$$D_3^2 t_3 = k \ln y_3$$

hence:

$$y_{13} = y_3^{(D_1/D_3)^2}$$

$$y_{23} = y_3^{(D_2/D_3)^2}$$

Figure 11:
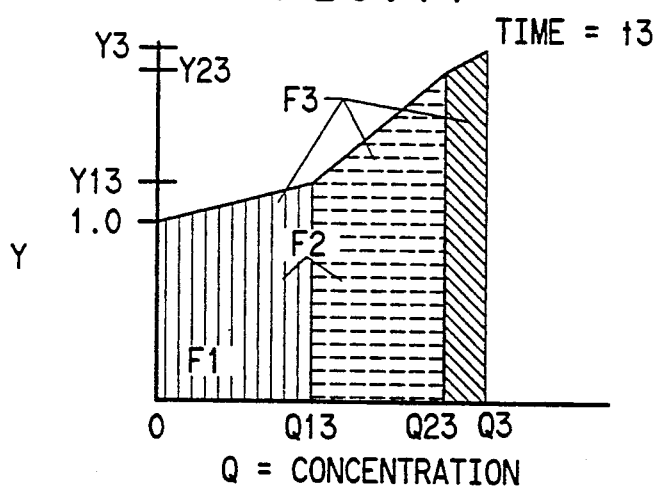

Also, equating areas (FIG. 11) gives:

$$F_1 = (1 + y_{13})Q_{13}/2$$

$$F_2 - F_1 = (y_{23} + y_{13})(Q_{23} - Q_{13})/2$$

$$F_3 - F_2 = (y_3 + y_{23})(Q_3 - Q_{23})/2$$

Eliminating $Q_{13}$ and $Q_{23}$ gives:

$$F_3 = (y_3 + y_{23}) Q_3/2 + \left[1 - \frac{y_3 + y_{23}}{y_{23} + y_{13}}\right] F_2 + \qquad \text{XIII}$$

-continued $$\left[\frac{y_3 + y_{23}}{y_{23} + y_{13}} - \frac{y_3 + y_{23}}{y_{13} + 1}\right] F_1$$

Proceeding in like manner gives the general formulas:

$$F_n - F_{n-1} = (y_n + y_{n-1,n})(Q_n - Q_{n-1})/2 \qquad \text{XIV}$$

$$F_{n-1} - F_{n-2} = (y_{n-1,n} + y_{n-2,n})(Q_{n-1,n} - Q_{n-2,n})/2 \qquad \text{XV}$$

and so on. By considering this series of equations with successive elimination of the Q functions, a general solution in recursive form may be obtained:

$$F_i = (y_i + y_{i-1,i}) Q_1/2 + \sum_{j=1}^{i-1}\left[\frac{y_i + y_{i-1,i}}{y_{j+1,i} + y_{j,i}} - \frac{y_i + y_{i-1,i}}{y_{j,i} + y_{j-1,i}}\right] F_j \qquad \text{IV}$$

where:

$$Y_{j,i} = y_i^{(D_j/D_i)^2}$$

$$y_{i,i} = y_i$$

$$Y_{0,i} = 1$$

Figure 12:
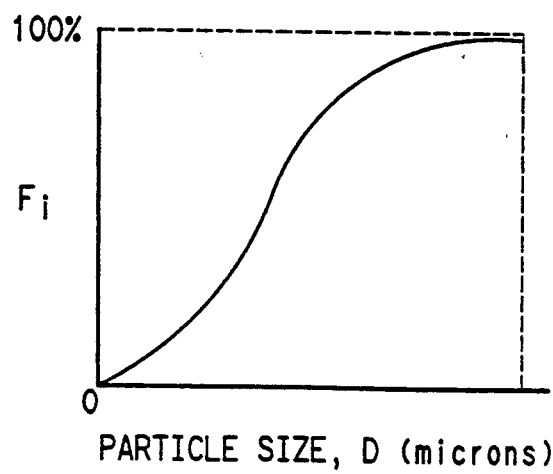
FIG. 12 is a-mass-undersize curve.

The values of $D_i$ and $F_i$ are then used to generate the mass undersize curve FIG. 12.

Figure 13:
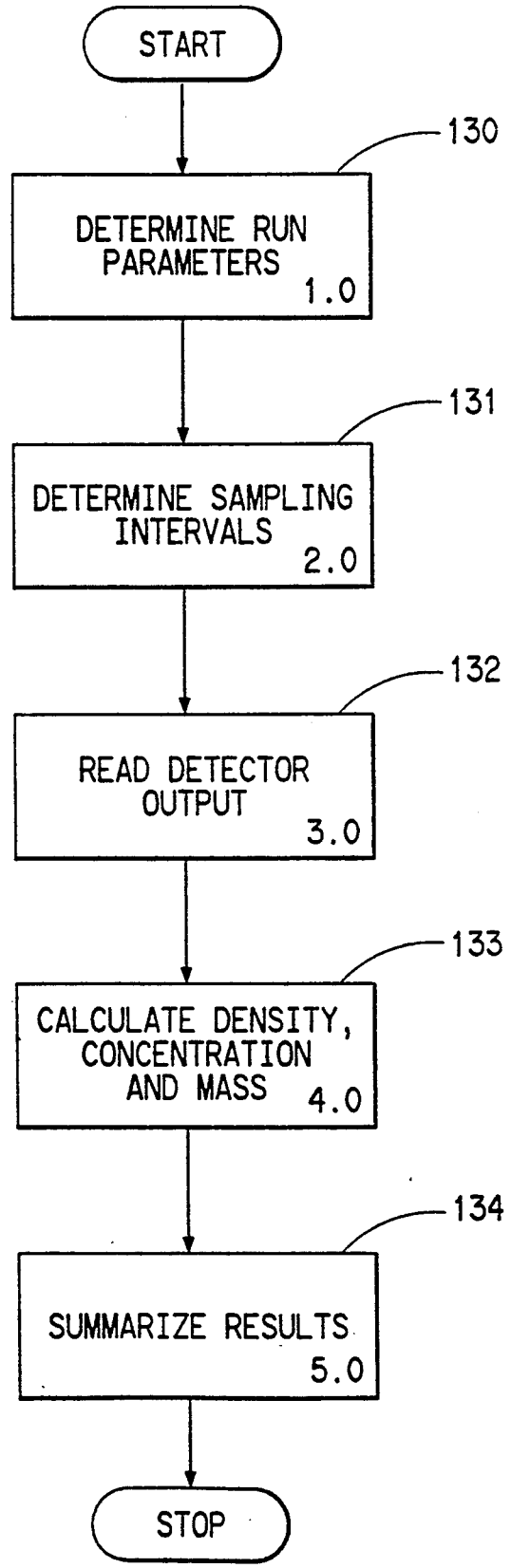
FIGS. 13-21A-B are flow diagrams representative of a software program which can be used to process the data.
Figure 14:
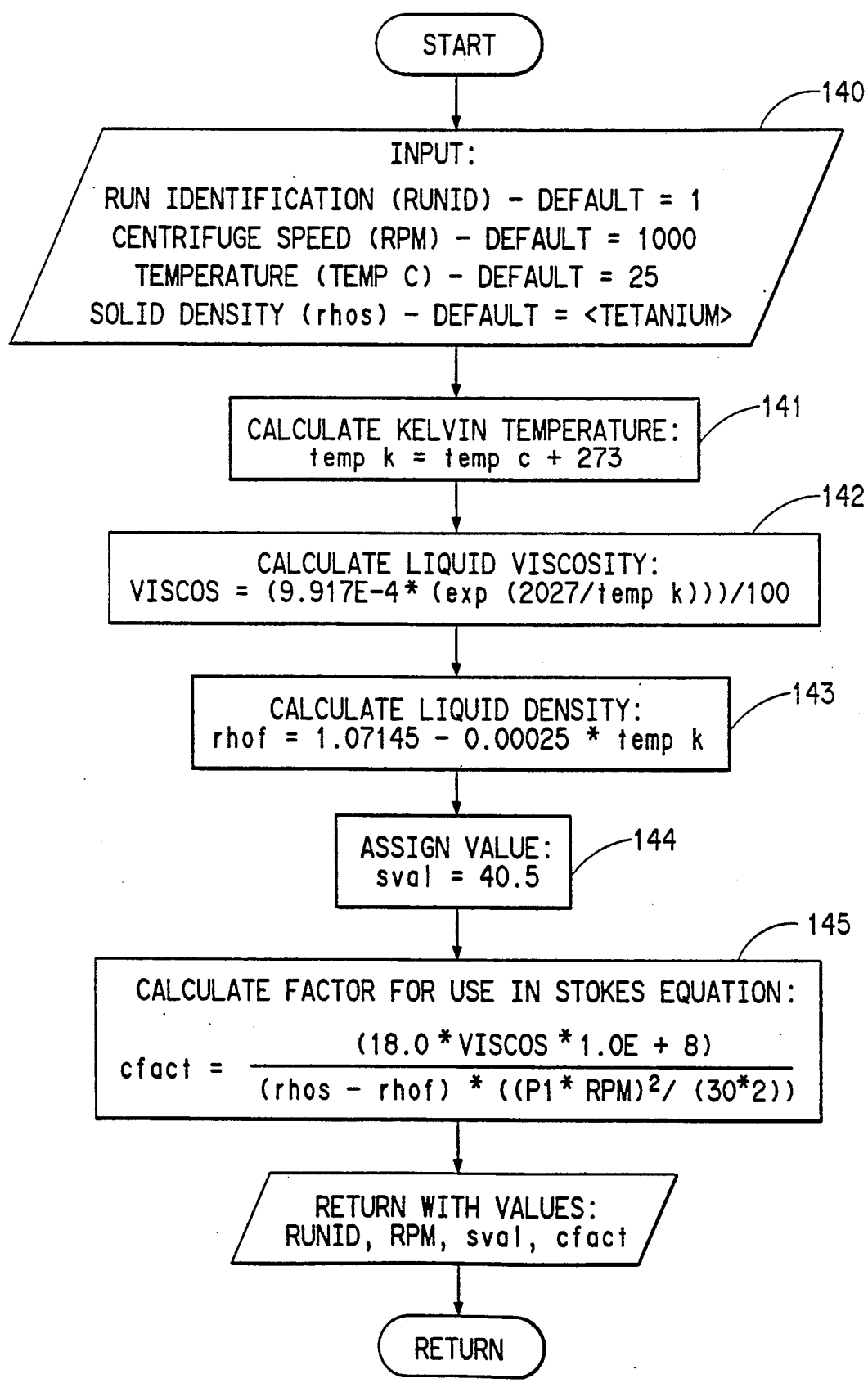

The general formulas developed above can be incorporated into a software program to speed the data analysis. The overall flow diagram for one such particle size analysis program is shown in FIG. 13, and is shown in more detail as FIGS. 14–21. The overall program FIG. 13 incorporates separate subroutines to determine run parameters at step 130, determine sampling intervals at step 131, read intensity output from the detector at step 132, calculate density, concentration and mass undersize values at step 133, and summarize results at step 134.

Figure 6:
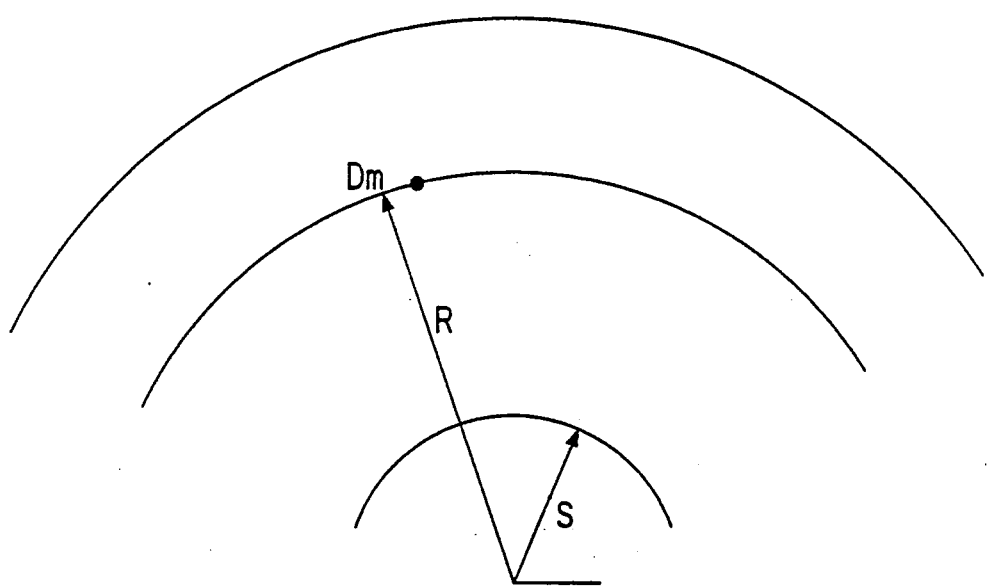
FIG. 6 is a representative slice of the settling tank.

In subroutine 1.0, the run paramaters are determined by the steps as shown in FIG. 1, several inputs are required at step 140: an identification for the run, the speed of the centrifuge, room temperature in degrees Celsius and the density of the solid undergoing analysis. A default value is assigned for each variable. Within the subroutine, the temperature is converted to degrees Kelvin at step 141, the viscosity of the liquid used for suspension is calculated at step 142, the density of the suspension liquid is calculated at step 143, and the value of s in centimeters at step 144 (see FIG. 6) is assigned. An intermediate calculation is carried out at step 145 yielding cfact, which will be used in a later subroutine to determine Stokes diameters. Although this embodiment of the subroutine assumes a known liquid, it would be a simple matter to modify the subroutine to request the specific type of liquid utilized and other information relevant thereto.

Figure 15:
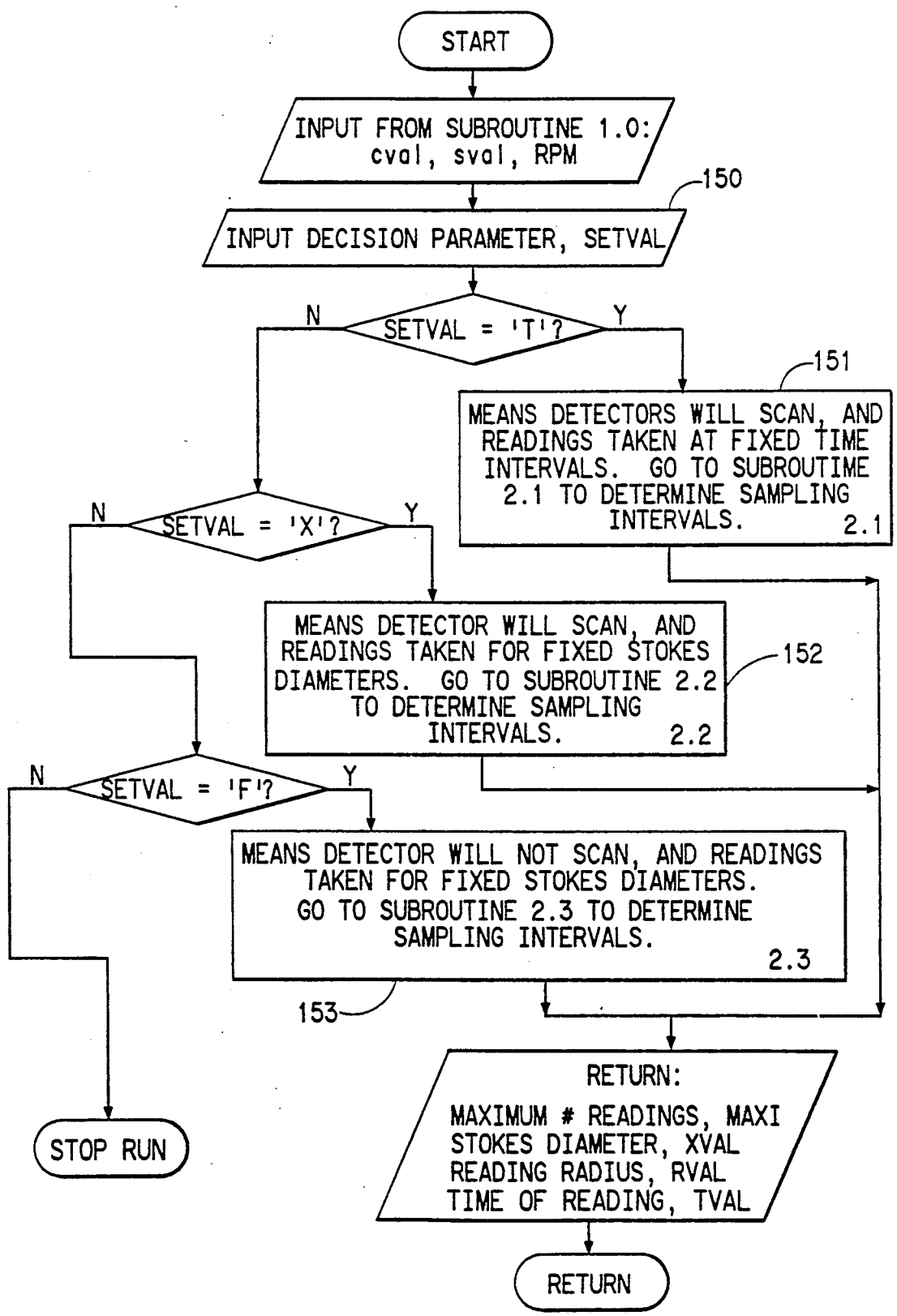
Figure 19:
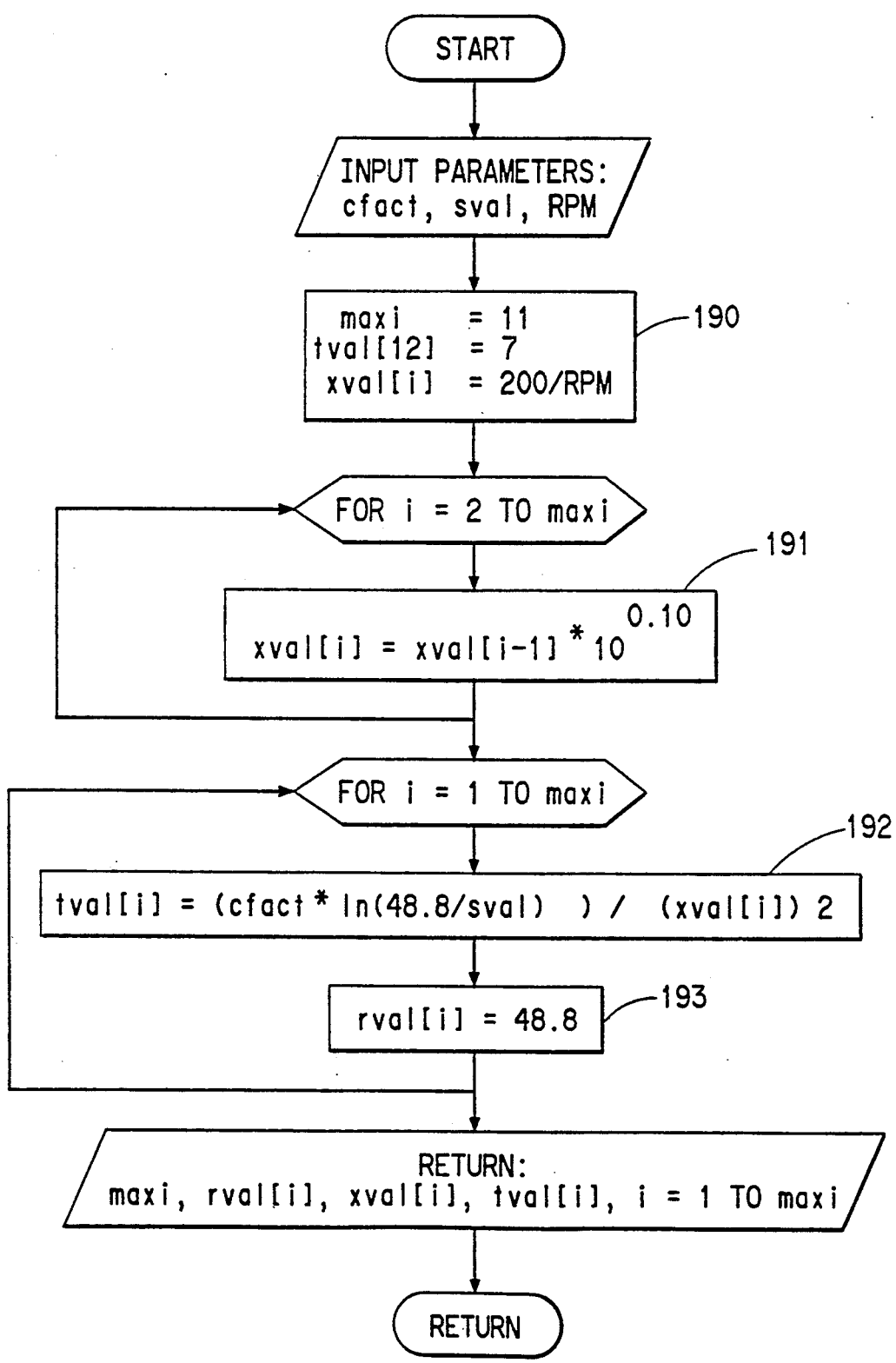

In subroutine 2.0, in which the sampling intervals are determined by the steps as shown in FIG. 15, a decision parameter, setval, is used at step 150 to indicate which of three types of analysis is desired. There is a choice of scanning detector and readings taken at fixed time intervals (step 151), scanning detector and readings taken at variable time intervals but fixed Stokes diameters (step 152), or fixed detector position and fixed Stokes diameters (step 153). If the mode desired is scanning detector/fixed time intervals (step 151), subroutine 2.1 (FIG. 16) is invoked. Selection of scanning detector/fixed Stokes diameter mode invokes subroutine 2.2 (FIG. 17), and selection of fixed detector/fixed Stokes diameter mode invokes subroutine 2.3 (FIG. 19). In each case, the maximum number of readings, Stokes diameter, radius and time of reading are calculated and returned to subroutine 2.0.

For a wide size distribution within a single sample, a geometric particle size interval is preferred, i.e., 1, 2, 4, 8, etc. For a narrow size distribution, an arithmetic particle size interval is preferred, i.e., 1, 2, 3, 4, etc. Choice of n is regulated by the resolution desired and the distribution expected. For a multimodal distribution, a high n value is preferred. For a wide distribution, a lower n is preferred which yields lower resolution and minimizes the effect of "noise."

Figure 16:
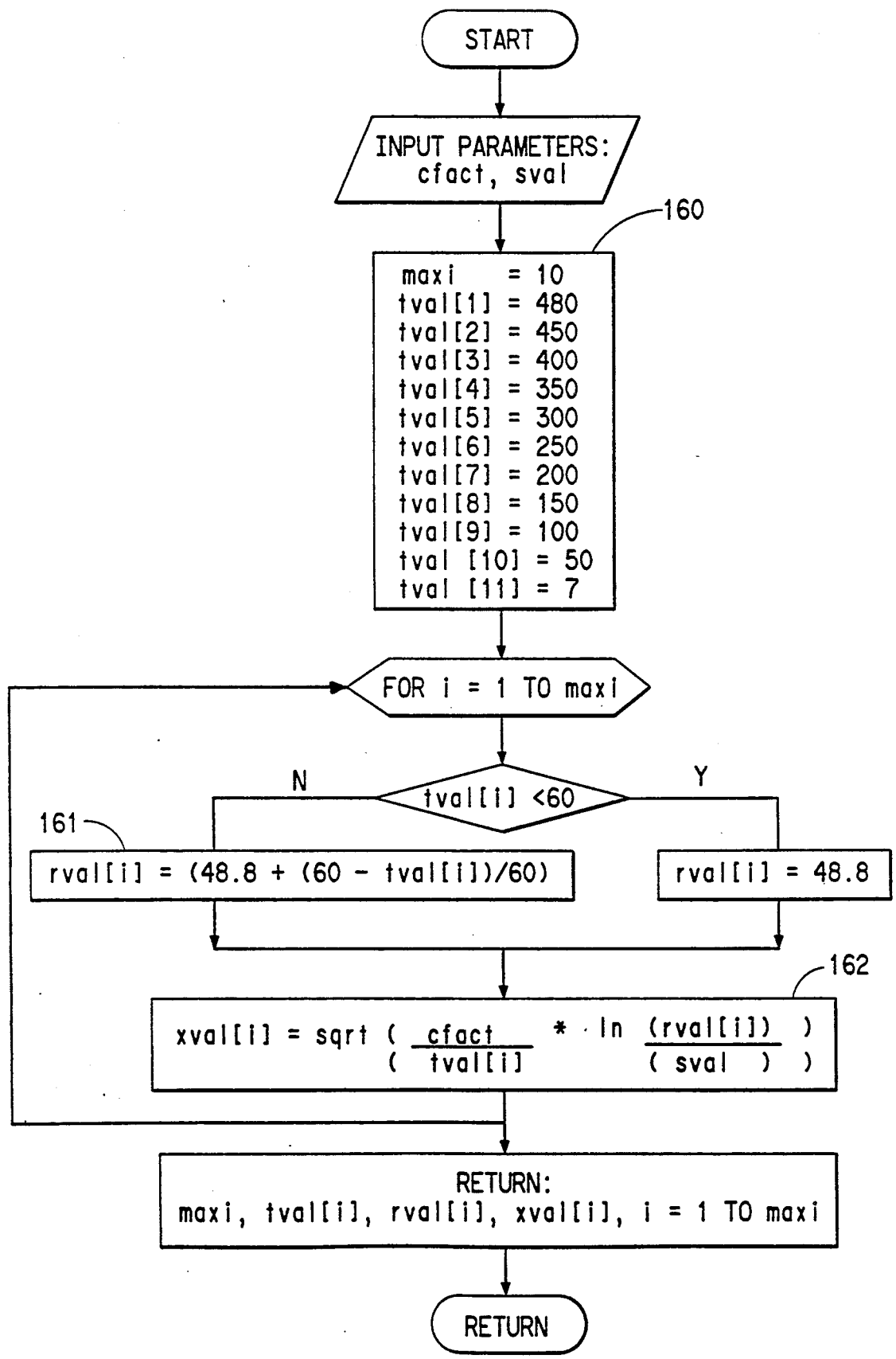

In subroutine 2.1, in which sampling intervals at fixed time intervals are determined while scanning as shown by the steps in FIG. 16 the number of readings, maxi, is assigned along with the time in seconds, tval(i) for each reading of step 160. Evaluation of PSD cannot commence until the analysis is completed, to refers to the last reading taken at 480 seconds, t2 to the eariler reading at 450 seconds and so on. The radius at which each reading is being taken, rval(i) is calculated at step 161 and is based upon the known rate of travel of the scanning assembly. The values of cfact, tval(i), rval(i) and sval are used to calculate the Stokes diameter, xval(i) at step 162 for each reading.

Providing means for varying scanning speed is possible and potentially useful, though, of course, it would add complication. A stepper motor could be used.

Figure 17:
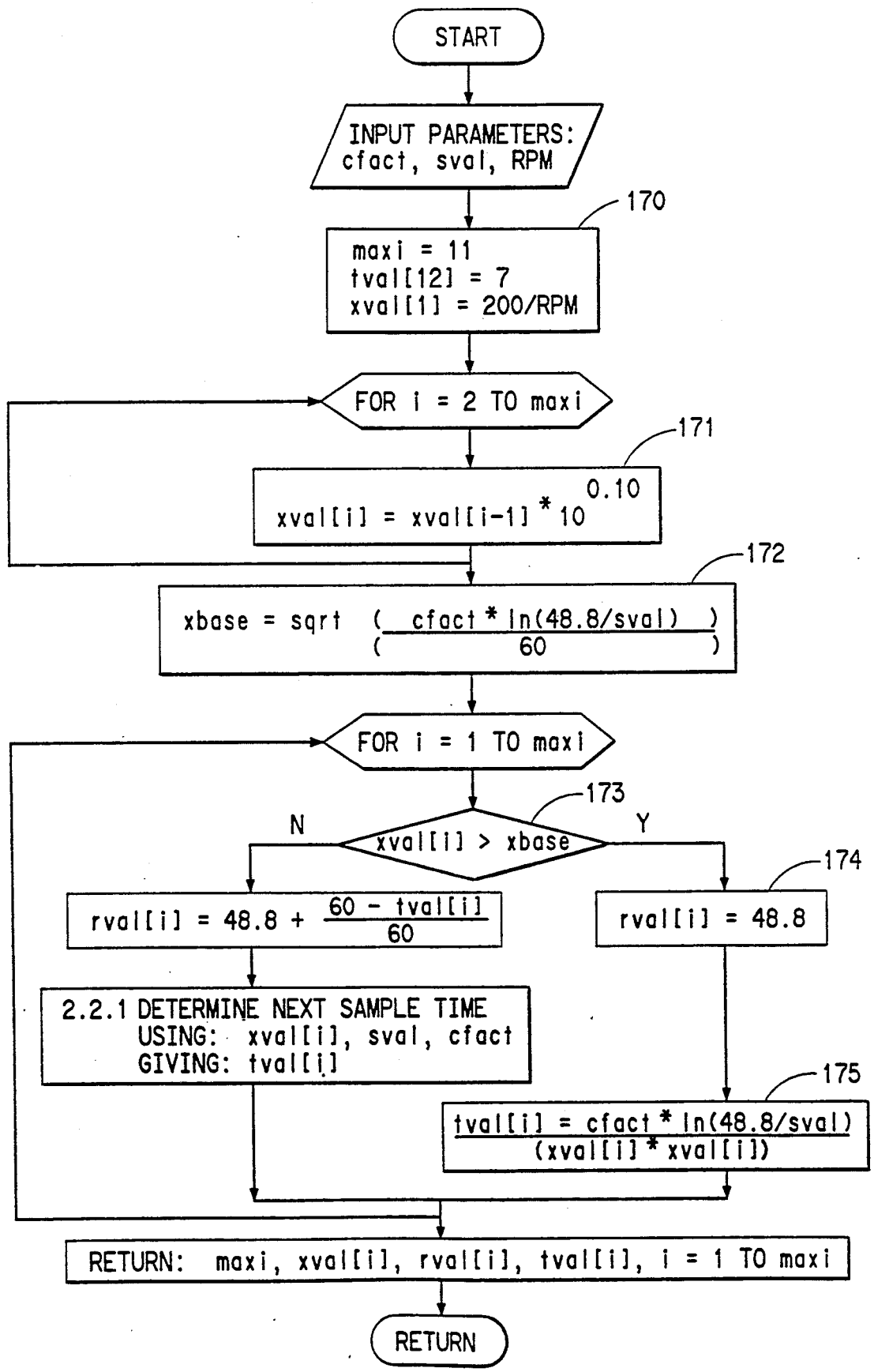
Figure 18:
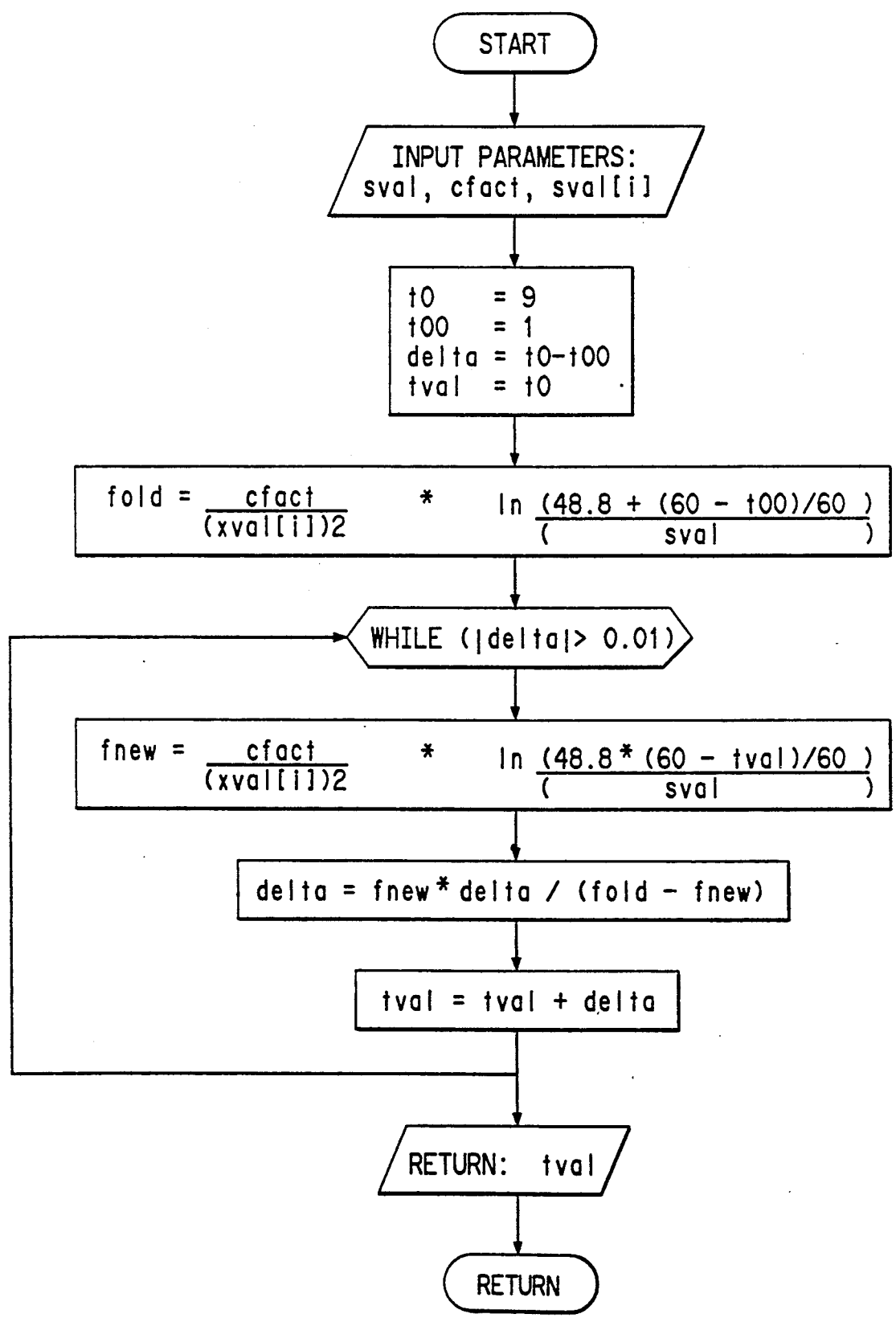

In subroutine 2.2, in which sampling intervals at fixed stokes diameters are determined while scanning as shown by the steps in FIG. 17 the number of readings, maxi, and the time for the final reading tval(12) are assigned and the desired Stokes diameter for the first reading xval(1) is calculated at step 170. The desired Stokes diameter for each of the remaining readings is calculated, xval(i) at step 171. The diameter of the largest particle in the measurement zone, xbase, is calculated at step 172. The calculated xval(i) values are each compared with the xbase value at step 173. A value of xval(i) greater than xbase indicates that the detector is at the innermost radial position rval(i)=48.8 cm at step 174. Using cfact, sval, xval(i) and sval, the time at which reading (rval(i), xval(i)) was taken is calculated at step 175. A value of xval(i) less than xbase indicates that the detector is at some radial position different than 48.8 cm, and the correct position r(i) is calculated at step 176. In this case, subroutine 2.2.1 (FIG. 18) is required to determine sampling time.

In subroutine 2.3 in which the sampling intervals at fixed stokes diameters without scanning are determined as shown by the steps in FIG. 19, the number of readings, maxi, and the time for the final reading tval(!2) are assigned and the desired Stokes diameter for the first reading xval(1) is calculated at step 180. The desired Stokes diameter for each of the remaining readings is calculated, xval(i), at step 191. The time of each reading, tval(i) is calculated at step 192 and the radial position is assigned for each reading, rval(i), at step 193. Note that the scanning system is not operational in this mode; the detector remains at a constant radial position.

Figure 20:
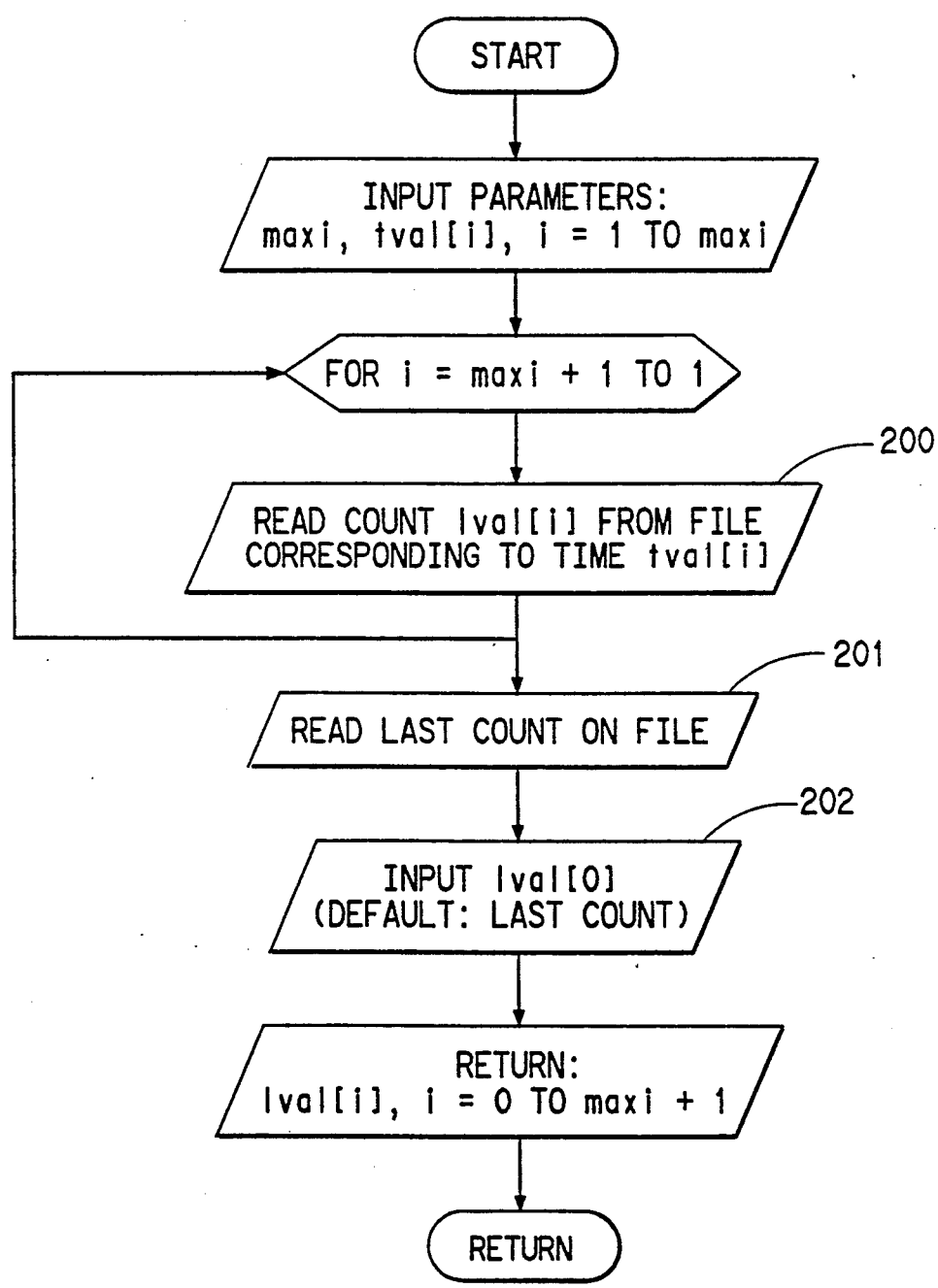

In subroutine 3.0 in which the sample deflection points are determined as shown by the steps in FIG. 20, the intensity readings, Ival(i), are read from a file for each of the times of interest, tval(i), at step 200. The last intensity reading on file is also read at step 201. If available, the intensity reading with clear liquid, Ival(0) is input. The default is the last reading available.

Figure 21A:
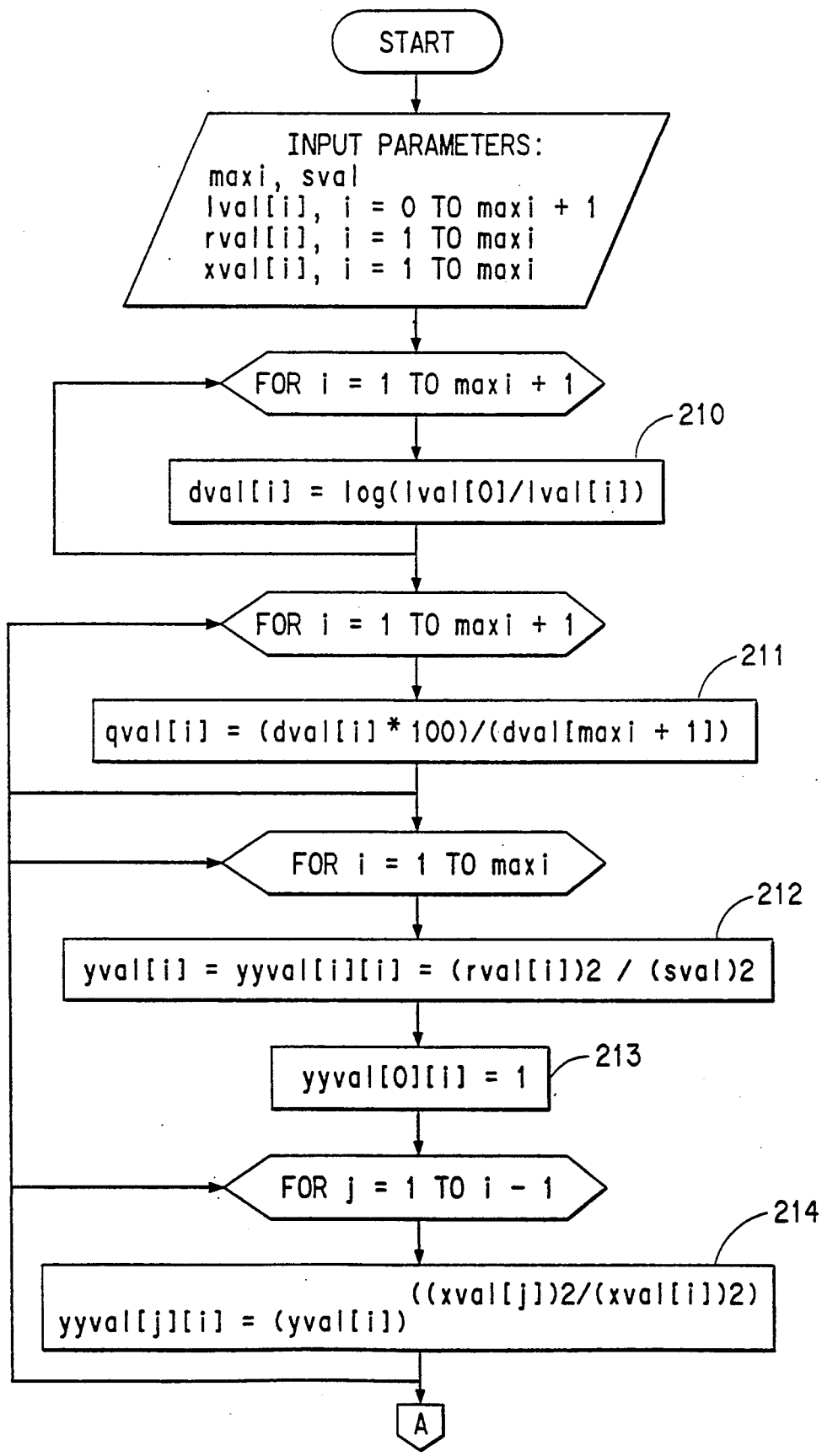
Figure 21B:
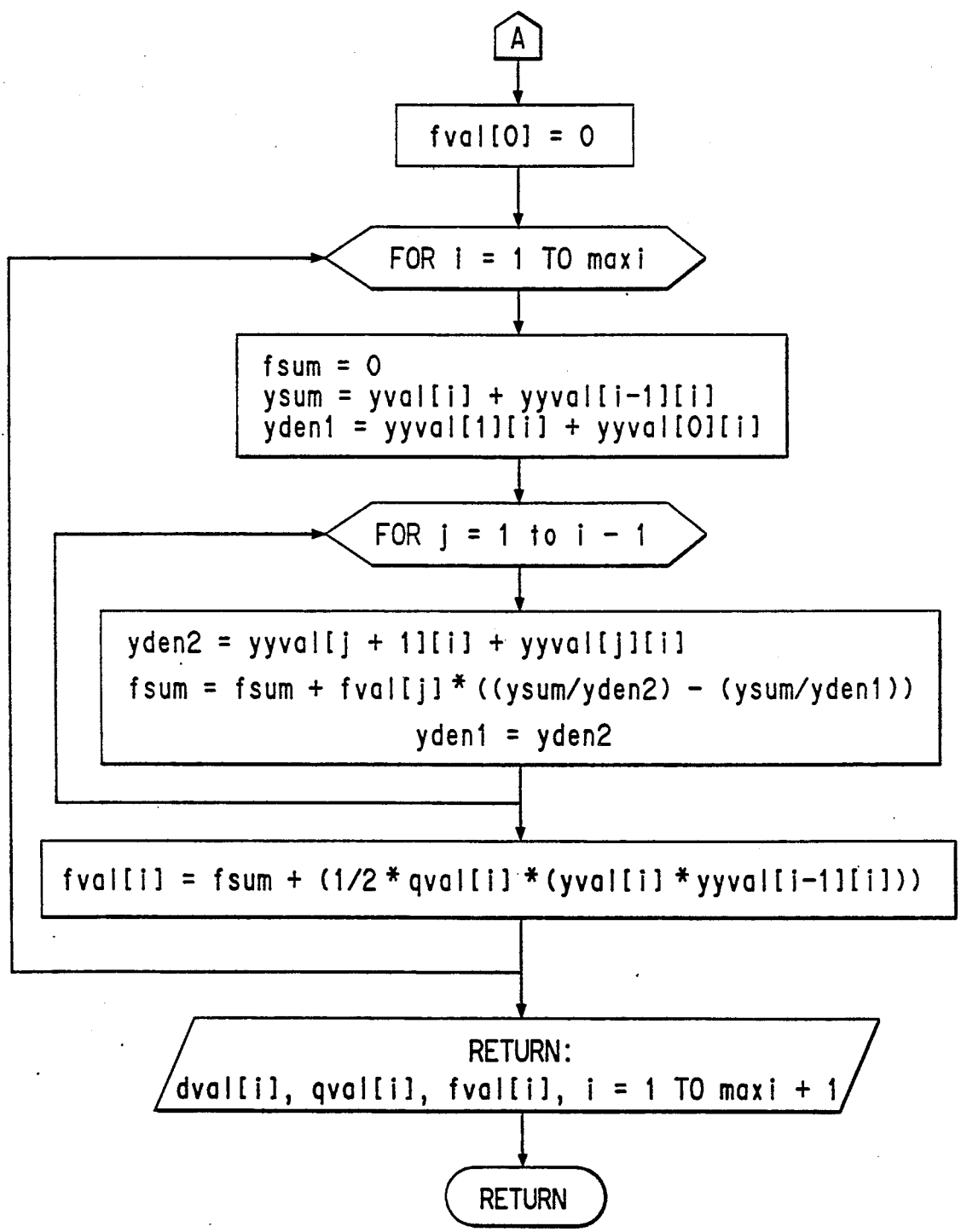

In subroutine 4.0 in which the density concentration and mass are determined as shown by the steps in FIGS. 21A and 21B, the concentration, qval(i), is calculated for each reading (see steps 210 and 211). These values correspond to the actual readings ($Q_1$, $Q_2$, etc.) on the horizontal axis Q in FIGS. 7-11. The related y values, yval(i) are also calculated at step 212. The boundary condition described earlier ($y_0, i1$) is assigned at step 213. The values corresponding to $y_{iii}$ are also calculated at step 213. The calculation of mass undersize by Equation IV is provided by the a culmination of steps 215, 216 and 217.

Other equivalent methods can be used to solve Equation IV, the above technique being merely exemplary.

Conventional printing and plotting techniques are utilized to tabulate the data and provide the mass undersize curve.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius and, unless otherwise indicated, all parts and percentages are by weight.

The entire text of all applications, patents and publications cited above are hereby incorporated by reference.

EXAMPLES

General Operation

The analysis begins with clear liquid, generally water. The water is injected into the rotating settling tank through a port located at the center of the disk. The detector is located at the outer radius of the measurement zone and the X-ray intensity is recorded. This provides the zero reading $I_c$ for the relationship set forth in Beers-Lambert law (Equation I). The values necessary to run the mass undersize software program; run identification, centrifuge speed, temperature, solid density, analysis mode, and X-ray intensity with clear liquid are entered. The bowl is stopped and emptied, the centrifuge is restarted and the suspension is added. The powder is premixed with suspension liquid, and is injected into the settling tank as a slurry thereby providing a homogeneous analysis. The analysis begins with the detector at the outermost radius of interest and scans slowly inward. Intensity readings are taken continually and saved in a file, so that whichever values are of interest are available. When the scan is complete, the software program calculates the values of Stokes diameter, measurement time, measurement radius, concentration and generates the Mass Undersize curve.

Example 1

A settling tank with internal radius of 5.2 cm and internal thickness of 2.5 cm is rotated with clear liquid at ambient temperature of 26° C. and a baseline X-ray beam intensity established. The water is emptied and a slurry of water with 0.1% Calgon ® dispersing agent 1 gram per liter) and titanium dioxide powder is injected. Centrifuge speed is set at 1,000 rpm. The X-ray detector assembly scans at a constant rate of 1.0 mm/minute for 7 minutes after a one minute pause beginning at R=4.8 cm. The time, radius and X-ray intensity values are recorded and Stokes diameter, density, concentration and mass percentage undersize are calculated.

Figure 22:
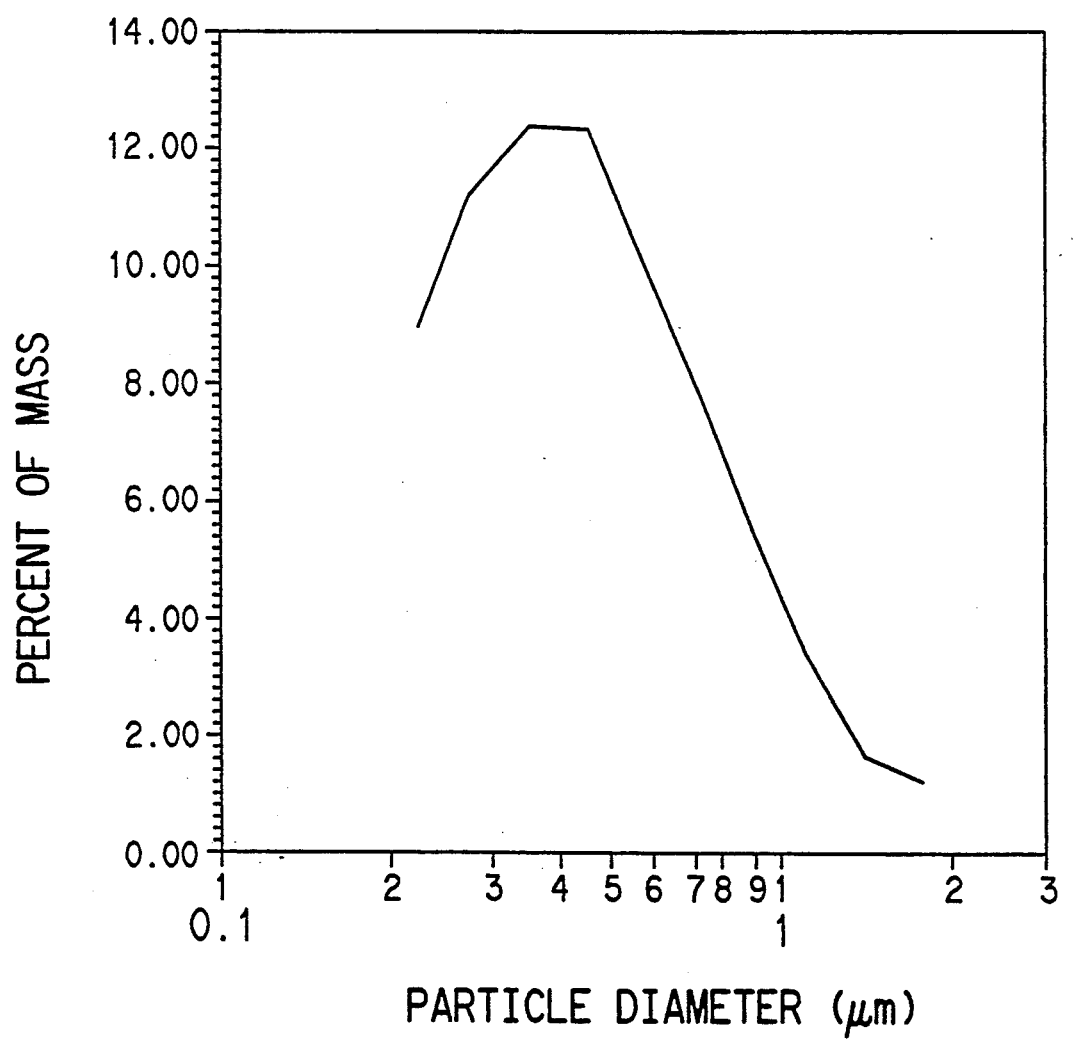
FIG. 22 is a graph of percent mass versus diameter.
Figure 23:
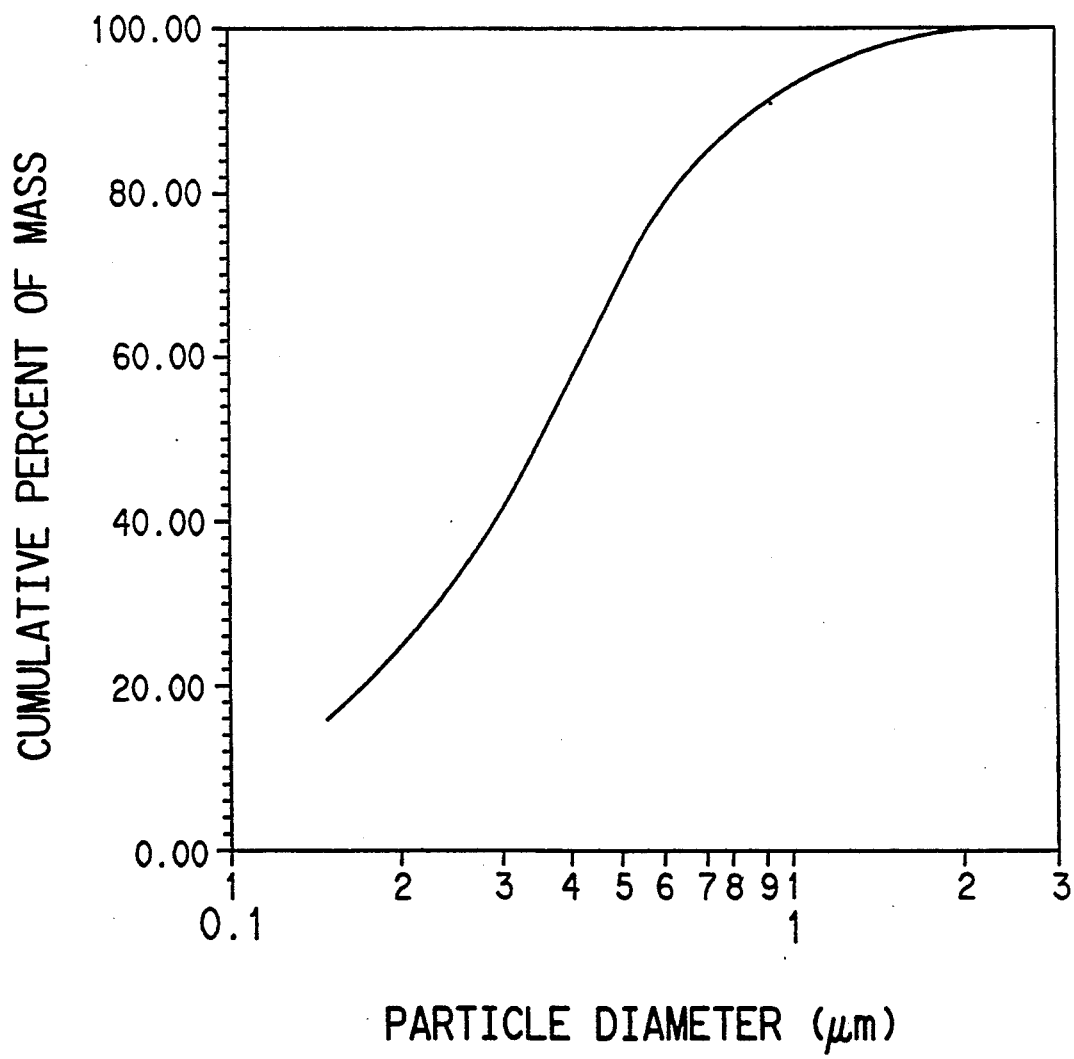
FIG. 23 is a graph of mass undersize versus diameter.

Using this data, the Percent Mass and Cumulative Percent mass (Mass Undersize) are calculated. The results are also plotted and are shown as FIGS. 22 and 23. At the end of the run, the settling tank is emptied and cleaned and the detector is reset to its original position. The entire test takes approximately 10 minutes.

TABLE I

X-Ray Scanning Centrifuge Analysis of Titanium Dioxide

N = 1000 rpm      $\rho_s$ = 4.26 g/cm³
$\eta$ = 0.01 poise      $\rho_f$ = 1.00 g/cm³
s = 39.5 mm

| i | $t_i$ (mins.) | $r_i$ (mm) | $D_m$ (microns) | $Q_i$ | $F_i$ | $F(D_m)$ (%) |
|---|---|---|---|---|---|---|
|   |   | 39.5 |   |   |   |   |
| 1 | 8 | 41.0 | 0.198 | 0 | 0 | 0 |
| 2 | 7 | 42.0 | 0.271 | 0.021 | 0.023 | 7.2 |
| 3 | 6 | 43.0 | 0.345 | 0.069 | 0.078 | 24.4 |
| 4 | 5 | 44.0 | 0.426 | 0.165 | 0.191 | 59.7 |
| 5 | 4 | 45.0 | 0.523 | 0.234 | 0.271 | 84.7 |
| 6 | 3 | 46.0 | 0.653 | 0.268 | 0.296 | 92.5 |
| 7 | 2 | 47.0 | 0.854 | 0.285 | 0.312 | 97.5 |
| 8 | 1 | 48.0 | 1.279 | 0.304 | 0.320 | 100.0 |
|   | 0 | 48.0 |   | 0.320 |   |   |

Tables I, II and III list the results of analysis on samples of titanium dioxide, barium titanate and lead ruthinate, respectively. The analysis on the barium titanate sample was performed in a non-scan mode.

TABLE II

X-Ray Scanning Centrifuge Analysis of Barium Titanate

N = 1000 rpm      Scan Off
$\eta$ = 0.00549 poise      r = 48.8 mm
$\rho_s$ = 6.0 g/cm³      s = 39.5 mm

| (i) | Time ($t_i$) (mins) | Size ($D_m$) (μm) | Counts per Second ($L_i$) | X-Ray Density ($Q_i$) | ($F_i$) | Mass (%) Undersize $F(D_m)$ |
|---|---|---|---|---|---|---|
| 0 |   |   | 76500 |   |   |   |
| 1 | 7 | 0.10 | 75502 | 0.0057 | 0.0072 | 10.4 |
| 2 | 6 | 0.141 | 75328 | 0.0067 | 0.0084 | 12.2 |
| 3 | 5 | 0.20 | 75103 | 0.0080 | 0.0095 | 13.8 |
| 4 | 4 | 0.282 | 74903 | 0.0092 | 0.0111 | 16.1 |
| 5 | 3 | 0.40 | 74430 | 0.0119 | 0.0145 | 21.0 |
| 6 | 2 | 0.564 | 73033 | 0.0201 | 0.0258 | 37.4 |
| 7 | 1 | 0.80 | 70563 | 0.0351 | 0.0463 | 67.2 |
|   | 0 |   | 65274 | 0.0689 |   |   |

$L_i$ is a measured intensity of emergent beam

TABLE III

X-Ray Scanning Centrifuge Analysis of Lead Ruthinate

N = 1000 rpm      $\rho_s$ = 39.5 mm
s = 39.5 mm      $\rho_f$ = 1.0 g/cm³
T = 23° C. [$\eta$ = 0.009325 poise]

| (i) | Time ($t_i$) (s) | Radius ($r_i$) (mm) | Size ($D_m$) (μm) | Counts per Second ($L_i$) | X-Ray Density ($Q_i$) | $F_i$ | Mass % Undersize $F(D_m)$ |
|---|---|---|---|---|---|---|---|
| 0 |   |   |   | 76500 |   |   |   |
| 1 | 480 | 41.8 | 0.151 | 75951 | 0.0031 | 0.0033 | 13.1 |
| 2 | 420 | 42.8 | 0.192 | 75727 | 0.0046 | 0.0047 | 18.7 |
| 3 | 360 | 43.8 | 0.236 | 75303 | 0.0069 | 0.0077 | 30.6 |
| 4 | 300 | 44.8 | 0.285 | 74854 | 0.0094 | 0.0106 | 42.1 |
| 5 | 240 | 45.8 | 0.346 | 74430 | 0.0119 | 0.0135 | 53.6 |
| 6 | 180 | 46.8 | 0.427 | 73931 | 0.0148 | 0.0169 | 67.1 |
| 7 | 120 | 47.8 | 0.555 | 73332 | 0.0184 | 0.0216 | 85.7 |

TABLE III-continued

X-Ray Scanning Centrifuge
Analysis of Lead Ruthinate

N = 1000 rpm $\quad \rho_s = 39.5$ mm
s = 39.5 mm $\quad \rho_f = 1.0$ g/cm$^3$
T = 23° C. [$\eta$ = 0.009325 poise]

| (i) | Time ($t_i$) (s) | Radius ($r_i$) (mm) | Size ($D_m$) (μm) | Counts per Second ($L_i$) | X-Ray Density ($Q_i$) | $F_i$ | Mass % Undersize $F(D_m)$ |
|---|---|---|---|---|---|---|---|
| 8 | 60 | 48.8 | 0.826 | 72534 | 0.0231 | 0.0252 | 100.0 |

Comparative Example A

Figure 24:
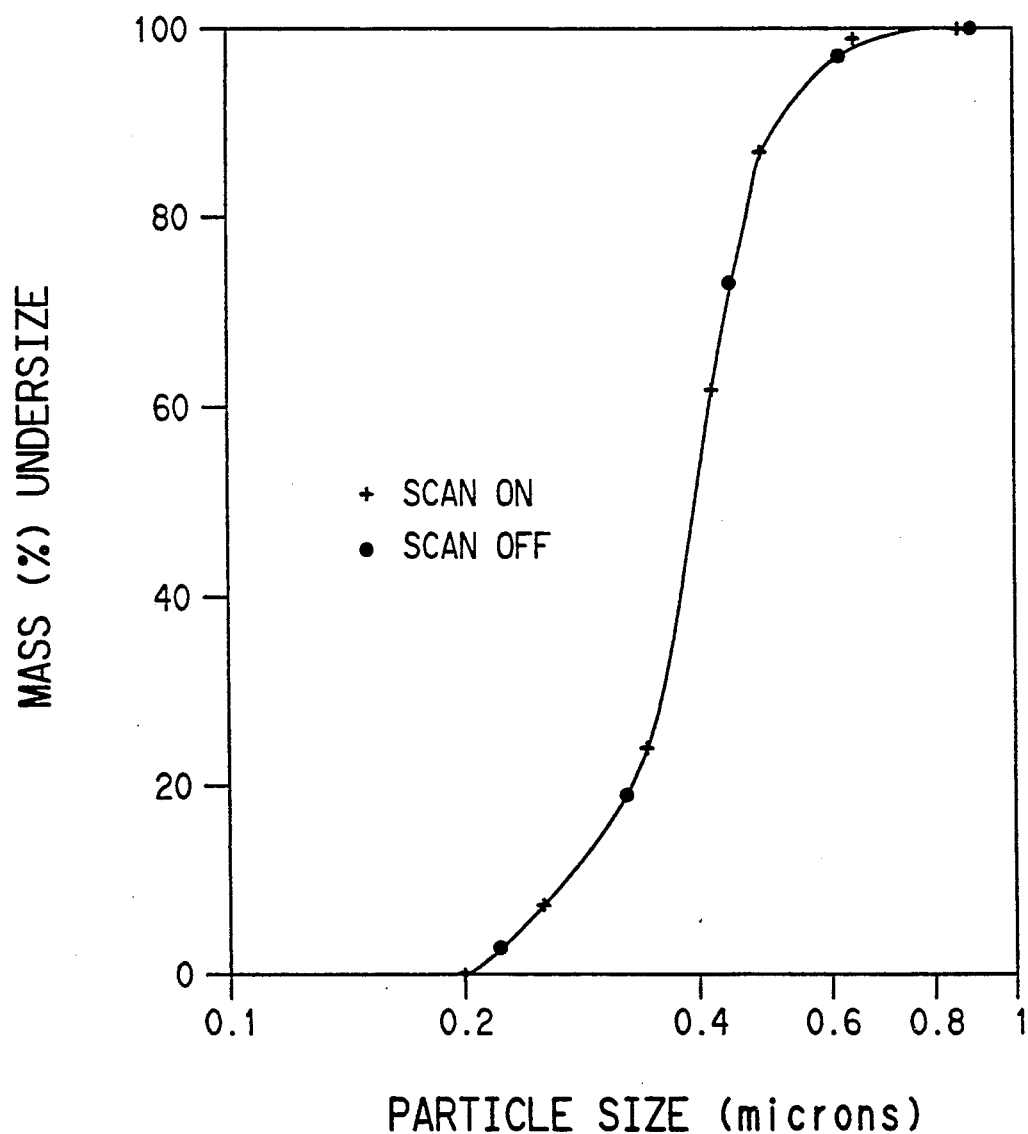
FIG. 24 is a comparative graph of mass undersize versus diameter for two different analytical methods.

Running a titanium dioxide sample in a non-scan mode and analyzing using conventional techniques requires approximately one hour. A sample was run in both non-scan mode and scan mode and the mass undersize is plotted for each in FIG. 24. As can be seen, the curves agree extremely well, indicating that no accuracy is lost in reducing the test time from one hour to 10 minutes through use of scanning along the radial direction.

Comparison of Settling Rates

A 1.0 micron and a 0.1 micron particle are allowed to settle from the surface, s, at 4 cm to a measurement zone at $r_i$=5 cm. For both cases $\eta$=0.01 poise (water), $\rho_s$=4.26 g/cm$^3$, $\rho_f$=1.00 g/cm$^3$, N=1,000 rpm, therefore, =100($\pi$/3) rad/sec.

For the 1 micron particle:

$$t = \frac{18 \times 0.01 \times \ln(5/4)}{3.26 \times (100 \times \pi/3)^2 \times (10^{-4})^2} = 112 \text{ seconds}$$

For the 0.1 micron particle:

$$t = 11235 \text{ seconds} = 187 \text{ minutes}$$

This 187 minutes settling time can be reduced by scanning so that the measurement radius falls from 5 cm to, say, 4.1 cm. In that case, the time changes to:

$$t = \frac{18 \times 0.01 \times \ln(4.1/4)}{3.26 \times (100 \times \pi/3)^2 \times (10^{-5})^2} = 21 \text{ minutes}$$

This illustrates the advantage of scanning regarding time considerations.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for determining the particle size distribution of a set of particles comprising,
    (a) measuring a parameter correlated with the concentration of particles in a sample of said particles which are settling, said parameter being measured at at least two different positions which lie along the direction of motion of said settling particles, wherein:
        (1) said parameter is the extent of X-ray transmission through said sample at said positions, and
        (2) said particles are settling under the influence of a gravitational force, centrifugal force or both, and
    (b) correlating said measurements with said particle size distribution.

2. A method of claim 1, wherein said particle sample is suspended in a rotating suspension fluid whereby the particles are subject to centrifugal force, and wherein said positions are along a direction radial to the axis of rotation of said fluid.

3. A method of claim 2, wherein each X-ray transmission measurement is at a different time and a different radial position.

4. A method of claim 2, wherein said measurements are correlated with particle size distribution in accordance with the following relationship:

$$F(D_m) = \int (r_i/s)^2 dQ$$

wherein
Q is the radiation density of the suspension at time $t_i$ and radius $r_i$,
$D_m$ is the largest particle diameter in the area of the beam at time $t_i$ and detection position $r_i$, and
$F(D_m)$ is the fractional mass smaller than $D_m$; and wherein $D_m$ and Q at $r_i$ are determined respectively, by the following equations:

$$I_t = I_c \exp(-Bc)$$

$$(D_m)^2 = \frac{18\eta \ln(r_i/s)}{(\rho_s - \rho_f) w^2 t_i}$$

wherein
$I_t$ is the measured intensity of the emerging beam;
$I_c$ is the intensity of the emerging beam when the settling tank is filled with a clear liquid;
c is the concentration of the particulate sample in the portion of the suspension which is within the area of the beam;
B is a constant;
$\rho_s$ is the density of the powdered material;
$\rho_f$ is the density of the liquid medium;
w is the radial velocity of the settling tank;
$\eta$ is the viscosity of the liquid medium;
s is the radial distance from the center of the settling tank to the surface of the suspension;
$r_i$ is the radial distance from the center of the disc-shaped settling tank to the point of detection at $t_i$; and
$t_i$ is the time of detection.

5. A method of claim 4, wherein said correlation is effected by a computer.

6. A method according to claim 4, wherein an X-ray tube source is used to supply said X-rays.

7. A method according to claim 6, wherein said X-ray tube source is a beryllium crystal and tungsten target assembly.

8. A method according to claim 4, wherein said particles are TiO$_2$ particles.

9. A method according to claim 1, wherein said particles have a particle size within the range of about 0.05 to 100 micrometers.

10. A method according to claim 4, wherein the fluid used to prepare the suspension of dispersed particles has a viscosity of about 0.5 centipoise to 1 poise.

11. A method according to claim 4, wherein the fluid medium used to prepare the suspension of dispersed particles has a density sufficient to permit particles to settle.

12. A method according to claim 4, wherein the suspension is contained in a rotating disc-shaped chamber.

13. A method according to claim 4, wherein said suspension of dispersed particles is a dispersion of $TiO_2$ particles in water.

14. A method according to claim 1, wherein said parameter is the extent of transmission of visible, infrared, ultraviolet, X-ray, gamma ray, electron beam or neutron beam radiation through said sample at said positions and times.

15. A method according to claim 1, wherein said particles settle due to the influence of a gravitational force and wherein the particles have a particle size within the range of about 1–80 micrometers.

16. A method according to claim 2, wherein said particles having a particle size within the range of about 0.10–10 micrometers.

17. A method according to claim 1, wherein the concentration of the particles in the suspension is sufficient to absorb or scatter at least about 10% of an incident beam of radiation.

18. A method according to claim 17, wherein the concentration of said particles in said suspension is sufficient to absorb or scatter about 20–30% of said incident beam of radiation.

19. A method according to claim 1, wherein the concentration of said particles in said suspension is about 0.01–4.0 vol.%.

20. A method according to claim 19, wherein the concentration of said particles in said suspension is about 0.1–3.0 vol.%.

21. A method according to claim 19, wherein the concentration of said particles in said suspension is about 0.1–1.0 volume percent.

22. A method according to claim 2, wherein the concentration of said particles in said suspension is sufficient to absorb or scatter about 10 percent of the incident beam of X-rays and wherein the concentration of said particles in said suspension is less than about 0.2 vol.%.

23. A method according to claim 1, wherein said parameter is the extent of transmission of visible, infrared, or ultraviolet radiation and the concentration of said particles in said suspension is about 0.01–0.1 vol.%.

24. A method according to claim 12, wherein said disc-shaped chamber is rotated at a speed of about 500–10,000 rpm.

25. A method of claim 2 for measuring particle size distribution comprising:

(a) radially scanning a suspension of dispersed particles under a centrifugal force field by passing a beam of radiation from a radiation source through said suspension while moving said radiation source and an associated radiation detector for receiving said beam in a radial direction with respect to said chamber, said radiation source and radiation detector being positioned on opposite sides of said chamber, and said radiation detector periodically generating radiation transmission data;

(b) delivering said data to a computer having stored therein a program for determining particle size distribution from said data; an (c) determining a mass undersize particle size distribution by said program in accordance with the relationship:

$$F(D_m) = \int (r_i/s)^2 dQ$$

wherein

Q is the radiation density of the suspension at time $t_i$ and radius $r_i$;

$D_m$ is the largest particle diameter in the area of the beam at time t and detection position $r_i$;

$F(D_m)$ is the fractional mass smaller than $D_m$, and wherein $D_m$ and Q at $r_i$ are determined, respectively, by the following equations:

$$I_t = I_c \exp(-Bc)$$

$$(D_m)^2 = \frac{18\eta \ln(r_i/s)}{(\rho_s - \rho_f) w^2 t_i}$$

wherein $I_t$ is the measured intensity of the emerging beam, $I_c$ is the intensity of the emerging beam when the settling tank is filled with a clear liquid, c is the concentration of the particulate sample in the portion of the suspension which is within the area of the beam, B is a constant, $\rho_s$ is the density of the powdered material, $\rho_f$ is the density of the liquid medium, w is the radial velocity of the settling tank, $\eta$ is the viscosity of the liquid medium, s is the radial distance from the center of the settling tank to the surface of the suspension, $r_i$ is the radial distance from the center of the disc-shaped settling tank to the point of detection at $t_i$, and $t_i$ is the time of detection.

26. A method according to claim 25, wherein the integral of step (c) is solved by the equation $$F_i = (y_i + y_{i-1,i}) Q_i/2 + \sum_{j=1}^{i-1} \left[ \frac{y_i + y_{i-1,i}}{y_{j+1,i} + y_{j,i}} - \frac{y_i + y_{i-1,i}}{y_{j,i} + y_{j-1,i}} \right] F_j$$

wherein $y_i$ is $(r_i/s)^2$;

$r_i$ is the radial distance to the point of detection at time $t_i$;

$y_{j,i}$ is $y_i^{(D_j/D_i)2}$ $y_{i,i}$ is $y_i$;

$y_{0,i}$ is 1;

$D_i$ is the largest particle diameter in the area of detection at position $r_i$ and time $t_i$;

n is the number of data points selected;

i is an integer from 1 to n; and $F_i$ is the percentage of mass of the particulate sample which has a diameter smaller than $D_i$.

27. A method according to claim 1, wherein said particles are settling under the influence of gravitational force, centrifugal force, or both.

28. A particle-size analyzer for determining the particle size distribution of a particulate sample of material, comprising:

(a) a rotatable sample vessel for retaining said sample in the form of a suspension of particles;

(b) a scanning assembly including a radiation source and an associated radiation detector, said assembly being movable in a direction radial with respect to the axis of rotation of said sample vessel, said radiation source and radiation detector being positioned on opposite sides of said sample vessel, whereby a beam of radiation generated by said radiation source can pass through said sample vessel and be detected by said radiation detector; and (c) a computer programmed to receive data from said radiation detector, and based thereon to calculate said particle size distribution according to the formula $$F(D_m) = \int (r_i/s)^2 dQ$$

wherein

Q is the radiation density of the suspension at time $t_i$ and radius $r_i$, $D_m$ is the largest particle diameter in the area of the beam at time t and detection position $r_i$, and $F(D_m)$ is the fractional mass smaller than $D_m$; and wherein $D_i$ and Q at $r_i$ are determined, respectively, by the following equations:

$$I_t = I_c \exp(-Bc)$$

$$(D_m)^2 = \frac{18\eta \ln(r_i/s)}{(\rho_s - \rho_f)w^2 t_i}$$

wherein $I_t$ is the measured intensity of the emerging beam of said radiation;

$I_c$ is the intensity of the emerging beam from said same settling tank except lacking said particles;

c is the concentration of the powder in the portion of the suspension which is within the area of the radiation beam;

B is a constant;

$\rho_s$ is the density of the powdered material;

$\rho_f$ is the density of the liquid medium;

w is the radial velocity of the settling tank;

$\eta$ is the viscosity of the liquid medium;

s is the radial distance from the center of the settling tank to the surface of the suspension;

$r_i$ is the radial distance from the center of the disc-shaped settling tank to the point of detection at $t_i$; and $t_i$ is the time of measurement.

29. An apparatus according to claim 28, wherein the formula $$F(D_m) = \int (r_i/s)^2 dQ$$

is solved by the equation $$F_i = (y_i + y_{i-1,i}) Q_i/2 + \sum_{j=1}^{i-1} \left[ \frac{y_i + y_{i-1,i}}{y_{j+1,i} + y_{j,i}} - \frac{y_i + y_{i-1,i}}{y_{j,i} + y_{j-1,i}} \right] F_j$$

wherein $y_i$ is $(r_i/s)^2$;

$r_i$ is the radial distance to the point of detection at time $t_i$;

$y_{j,i}$ is $y_i^{(D_j/D_i)2}$ $y_{i,i}$ is $y_i$;

$y_{0,i}$ is 1;

$D_i$ is the largest particle diameter in the area of detection at position $r_i$ and time $t_i$;

n is an integer;

i is an integer from 1 to n; and $F_i$ is the percentage of mass of the particulate sample which has a diameter smaller than $D_i$.

30. An apparatus according to claim 28, wherein said radiation source is an X-ray source.

31. An apparatus according to claim 30, wherein said radiation source is a beryllium crystal and tungsten target assembly.

32. A particle size analyzer according to claim 28, wherein said rotatable sample vessel is manufactured from material exhibiting a beam transmission of more than 50 percent with respect to the radiation delivered from said radiation source.

33. A particle size analyzer of claim 28, wherein said rotatable sample vessel is manufactured from acrylic, polyvinylacetate, polyethylene, or polyvinylchloride.

* * * * *